US011930087B1

(12) United States Patent
Jain et al.

(10) Patent No.: US 11,930,087 B1
(45) Date of Patent: Mar. 12, 2024

(54) MATCHING PATIENTS WITH DECENTRALIZED CLINICAL TRIALS TO IMPROVE ENGAGEMENT AND RETENTION

(71) Applicant: VigNet Incorporated, Fairfax, VA (US)

(72) Inventors: Praduman Jain, Fairfax, VA (US); Josh Schilling, Salem, OR (US); Dave Klein, Oakton, VA (US)

(73) Assignee: VigNet Incorporated, Fairfax, VA (US)

( * ) Notice: Subject to any disclaimer, the term of this patent is extended or adjusted under 35 U.S.C. 154(b) by 0 days.

(21) Appl. No.: 17/588,739

(22) Filed: Jan. 31, 2022

Related U.S. Application Data

(63) Continuation of application No. 17/163,336, filed on Jan. 29, 2021, now Pat. No. 11,240,329.

(51) Int. Cl.
*H04L 67/125* (2022.01)
*G16H 20/00* (2018.01)
(Continued)

(52) U.S. Cl.
CPC .......... *H04L 67/535* (2022.05); *G16H 20/00* (2018.01); *G16H 50/30* (2018.01); *H04L 67/125* (2013.01); *H04L 67/306* (2013.01); *H04L 67/34* (2013.01)

(58) Field of Classification Search
None
See application file for complete search history.

(56) References Cited

U.S. PATENT DOCUMENTS 5,547,878 A    8/1996   Kell
6,029,144 A    2/2000   Barrett et al.
(Continued)

FOREIGN PATENT DOCUMENTS

CN    106384321    2/2017
EP    2851820    3/2015
(Continued)

OTHER PUBLICATIONS

U.S. Notice of Allowance in U.S. Appl. No. 17/224,315, dated Dec. 9, 2022, 11 pages.
(Continued)

*Primary Examiner* — James A Edwards
(74) *Attorney, Agent, or Firm* — Fish & Richardson P.C.

(57) ABSTRACT

In some implementations, a system includes a database comprising program data for each of a plurality of programs that involve monitoring using remote devices. The system includes a server system configured to selectively distribute the configuration data for the respective programs to remote devices over a communication network and monitor incoming data received from the remote devices over the communication network to determine changes to programs active for the remote devices. The server system can be configured to collect, from the respective remote devices, monitoring data that is generated by the programs active for the remote devices and is provided over the communication network. The server system can compare the collected monitoring data with reference levels, select one or more program changes, and distribute, to various remote devices, data indicating appropriate program changes for the remote devices.

20 Claims, 14 Drawing Sheets

(51) Int. Cl.
  *G16H 50/30* (2018.01)
  *H04L 67/00* (2022.01)
  *H04L 67/306* (2022.01)
  *H04L 67/50* (2022.01)

(56) References Cited

U.S. PATENT DOCUMENTS

| | | |
|---|---|---|
| 6,321,172 B1 | 11/2001 | Jakob et al. |
| 6,514,200 B1 | 2/2003 | Khouri |
| 6,663,846 B1 | 12/2003 | McCombs et al. |
| 6,879,970 B2 | 4/2005 | Shiffman et al. |
| 7,054,782 B2 | 5/2006 | Hartlaub |
| 7,251,609 B1 | 7/2007 | McAlindon et al. |
| 7,415,447 B2 | 8/2008 | Shiffman et al. |
| 7,752,059 B2 | 7/2010 | Sweeney et al. |
| 7,853,455 B2 | 12/2010 | Brown |
| 8,056,100 B2 | 11/2011 | Herz et al. |
| 8,065,180 B2 | 11/2011 | Hufford et al. |
| 8,180,688 B1 | 5/2012 | Velummylum et al. |
| 8,380,531 B2 | 2/2013 | Paty et al. |
| 8,433,605 B2 | 4/2013 | Hufford et al. |
| 8,533,029 B2 | 9/2013 | Hufford et al. |
| 8,775,415 B2 | 7/2014 | Jeon et al. |
| 8,805,759 B1 | 8/2014 | Cha et al. |
| 8,990,250 B1 | 3/2015 | Chowdry et al. |
| 9,361,011 B1 | 6/2016 | Burns |
| 9,426,433 B1 | 8/2016 | Mazzarella |
| 9,461,972 B1 | 10/2016 | Mehta |
| 9,542,649 B2 | 1/2017 | Su |
| 9,753,618 B1 * | 9/2017 | Jain .................. G09B 7/02 |
| 9,824,606 B2 | 11/2017 | Basson et al. |
| 9,848,061 B1 | 12/2017 | Jain et al. |
| 9,858,063 B2 | 1/2018 | Jain et al. |
| 9,928,230 B1 | 3/2018 | Jain et al. |
| 9,942,358 B2 | 4/2018 | Babu et al. |
| 9,983,775 B2 | 5/2018 | Jain et al. |
| 10,002,199 B2 | 6/2018 | Matamala et al. |
| 10,068,422 B2 | 9/2018 | Gadher et al. |
| 10,069,934 B2 | 9/2018 | Jain et al. |
| 10,095,688 B1 | 10/2018 | Jain et al. |
| 10,152,761 B2 | 12/2018 | Kress et al. |
| 10,304,000 B2 | 5/2019 | Birnbaum et al. |
| 10,311,478 B2 | 6/2019 | Dai et al. |
| 10,521,557 B2 | 12/2019 | Jain et al. |
| 10,565,894 B1 | 2/2020 | Jain et al. |
| 10,733,266 B2 | 8/2020 | Whitehurst |
| 10,756,957 B2 | 8/2020 | Jain et al. |
| 10,762,990 B1 | 9/2020 | Jain et al. |
| 10,938,651 B2 | 3/2021 | Jain et al. |
| 11,056,242 B1 | 7/2021 | Jain et al. |
| 11,061,798 B1 | 7/2021 | Jain et al. |
| 11,082,487 B1 | 8/2021 | Jain et al. |
| 11,102,304 B1 | 8/2021 | Jain et al. |
| 11,296,971 B1 | 4/2022 | Jain et al. |
| 11,321,115 B2 | 5/2022 | Thakur et al. |
| 11,361,846 B1 | 6/2022 | Jain et al. |
| 11,417,418 B1 | 8/2022 | Jain et al. |
| 11,474,800 B2 | 10/2022 | Jain et al. |
| 11,507,737 B1 | 11/2022 | Jain et al. |
| 11,636,500 B1 | 4/2023 | Jain et al. |
| 11,645,180 B1 | 5/2023 | Jain et al. |
| 2001/0019338 A1 | 9/2001 | Roth |
| 2002/0022973 A1 | 2/2002 | Sun |
| 2002/0099570 A1 | 7/2002 | Knight |
| 2002/0143595 A1 | 10/2002 | Frank et al. |
| 2003/0065669 A1 | 4/2003 | Kahn et al. |
| 2003/0130871 A1 | 7/2003 | Rao et al. |
| 2004/0122715 A1 | 6/2004 | McAuliffe |
| 2004/0172447 A1 | 9/2004 | Miller |
| 2004/0210457 A1 | 10/2004 | Sameh |
| 2005/0086587 A1 | 4/2005 | Balz |
| 2005/0165626 A1 | 7/2005 | Karpf |
| 2005/0186550 A1 | 8/2005 | Gillani |
| 2006/0004603 A1 | 1/2006 | Peterka et al. |
| 2006/0107219 A1 | 5/2006 | Ahya |
| 2006/0184493 A1 | 8/2006 | Shiffman et al. |
| 2007/0072156 A1 | 3/2007 | Kaufman et al. |
| 2007/0136093 A1 | 6/2007 | Rankin et al. |
| 2007/0179361 A1 | 8/2007 | Brown et al. |
| 2007/0250429 A1 | 10/2007 | Walser et al. |
| 2008/0005679 A1 | 1/2008 | Rimas-Ribikauskas |
| 2008/0010254 A1 | 1/2008 | Settimi |
| 2008/0127040 A1 | 5/2008 | Barcellona |
| 2008/0140444 A1 | 6/2008 | Karkanias |
| 2008/0195600 A1 | 8/2008 | Deakter |
| 2009/0024944 A1 | 1/2009 | Louch |
| 2009/0043689 A1 | 2/2009 | Yang |
| 2009/0163182 A1 | 6/2009 | Gatti |
| 2009/0172002 A1 | 7/2009 | Bathiche |
| 2010/0036681 A1 | 2/2010 | Naik et al. |
| 2010/0041378 A1 | 2/2010 | Aceves |
| 2010/0088245 A1 | 4/2010 | Harrison et al. |
| 2010/0218132 A1 | 8/2010 | Soni et al. |
| 2010/0250258 A1 | 9/2010 | Smithers et al. |
| 2011/0145747 A1 | 6/2011 | Wong et al. |
| 2011/0200979 A1 | 8/2011 | Benson |
| 2011/0288900 A1 | 11/2011 | McQueen et al. |
| 2012/0035954 A1 | 2/2012 | Yeskel |
| 2012/0072232 A1 | 3/2012 | Frankham et al. |
| 2012/0102050 A1 | 4/2012 | Button |
| 2012/0272156 A1 | 10/2012 | Kerger |
| 2013/0110565 A1 | 5/2013 | Means |
| 2013/0145024 A1 | 6/2013 | Cao |
| 2013/0166494 A1 | 6/2013 | Davis |
| 2013/0238686 A1 | 9/2013 | O'Donoghue |
| 2013/0326375 A1 | 12/2013 | Barak et al. |
| 2014/0017648 A1 | 1/2014 | Williams et al. |
| 2014/0088995 A1 | 3/2014 | Damani |
| 2014/0100883 A1 | 4/2014 | Hamilton |
| 2014/0156645 A1 | 6/2014 | Brust |
| 2014/0156823 A1 | 6/2014 | Liu |
| 2014/0157171 A1 | 6/2014 | Brust et al. |
| 2014/0181715 A1 | 6/2014 | Axelrod |
| 2014/0240122 A1 | 8/2014 | Roberts |
| 2014/0273913 A1 | 9/2014 | Michel |
| 2014/0344397 A1 | 11/2014 | Kostof |
| 2015/0006214 A1 | 1/2015 | Lavoie et al. |
| 2015/0012301 A1 | 1/2015 | Weschler et al. |
| 2015/0088955 A1 | 3/2015 | Hendrick et al. |
| 2015/0106449 A1 | 4/2015 | Cherry |
| 2015/0135160 A1 | 5/2015 | Gauvin |
| 2015/0148061 A1 | 5/2015 | Koukoumidis |
| 2015/0178473 A1 | 6/2015 | Hufford et al. |
| 2015/0178474 A1 | 6/2015 | Hufford et al. |
| 2015/0286802 A1 | 10/2015 | Kansara |
| 2016/0058287 A1 | 3/2016 | Dyell |
| 2016/0085754 A1 | 3/2016 | Gifford et al. |
| 2016/0196389 A1 | 7/2016 | Moturu et al. |
| 2016/0300570 A1 | 10/2016 | Gustafson et al. |
| 2016/0357794 A1 | 12/2016 | Liang et al. |
| 2016/0357944 A1 | 12/2016 | Iyer et al. |
| 2017/0024546 A1 | 1/2017 | Schmidt |
| 2017/0097743 A1 | 4/2017 | Hameed et al. |
| 2017/0154166 A1 | 6/2017 | Klein et al. |
| 2017/0169343 A1 | 6/2017 | Kirkham et al. |
| 2017/0118159 A1 | 7/2017 | Ratiu et al. |
| 2017/0228229 A1 | 8/2017 | Jain et al. |
| 2017/0293923 A1 * | 10/2017 | Margolis ............ G06Q 30/0204 |
| 2017/0308680 A1 | 10/2017 | Efros et al. |
| 2018/0046780 A1 | 2/2018 | Graiver et al. |
| 2018/0056130 A1 | 3/2018 | Bitran et al. |
| 2018/0090229 A1 | 3/2018 | Sanyal |
| 2018/0114596 A1 | 4/2018 | Churchwell et al. |
| 2018/0122509 A1 | 5/2018 | Christiansson |
| 2018/0150523 A1 | 5/2018 | Shiffman et al. |
| 2018/0176331 A1 | 6/2018 | Jain et al. |
| 2018/0206775 A1 | 7/2018 | Saria et al. |
| 2018/0286509 A1 | 10/2018 | Shah |
| 2018/0301205 A1 | 10/2018 | Mao |
| 2018/0365316 A1 | 12/2018 | Liang et al. |
| 2019/0068753 A1 | 2/2019 | Jain et al. |
| 2019/0207814 A1 * | 7/2019 | Jain .................. G16H 40/67 |
| 2019/0306093 A1 | 10/2019 | Schilling et al. |
| 2020/0035341 A1 | 1/2020 | Kain et al. |

(56) References Cited

U.S. PATENT DOCUMENTS

| | | |
|---|---|---|
| 2020/0131581 A1 | 4/2020 | Jain et al. |
| 2020/0243167 A1 | 7/2020 | Will et al. |
| 2020/0250508 A1 | 8/2020 | De Magalhaes |
| 2020/0303074 A1 | 9/2020 | Mueller-Wolf |
| 2020/0336450 A1 | 10/2020 | Gao et al. |
| 2021/0004692 A1 | 1/2021 | Ferrara et al. |
| 2021/0058490 A1 | 2/2021 | Jain |

FOREIGN PATENT DOCUMENTS

| | | |
|---|---|---|
| WO | WO1995012812 | 5/1995 |
| WO | WO2013144769 | 10/2013 |

OTHER PUBLICATIONS

Final Office Action in U.S. Appl. No. 15/040,635, dated Apr. 13, 2017, 13 pages.

Final Office Action in U.S. Appl. No. 15/152,411, dated Mar. 17, 2017, 17 pages.

Final Office Action in U.S. Appl. No. 16/120,083, dated Jan. 13, 2021, 17 pages.

Final Office Action in U.S. Appl. No. 17/146,473, dated Jul. 7, 2021, 41 pages.

Final Office Action in U.S. Appl. No. 16/800,952, dated Jan. 19, 2021, 24 pages.

Goldsack et al., "Verification, analytical validation and clinical validation (V3): the foundation of determining fit-for-purpose for Biometric Monitoring Technologies (BioMeTs)", NPJ Digital Medicine, Apr. 14, 2020, 3(55):1-15.

http://www.khanacademic.org, 2017, 1 page.

Kotsiantis, "Supervised Machine Learning: A Review of Classification Techniques", Informatica 31, Jul. 2007, pp. 249-268.

Non-Final Office Action in U.S. Appl. No. 15/040,635, dated Dec. 30, 2016, 11 pages.

Non-Final Office Action in U.S. Appl. No. 15/040,635, dated Jul. 8, 2016, 9 pages.

Non-Final Office Action in U.S. Appl. No. 15/067,046, dated Nov. 1, 2016, 19 pages.

Non-Final Office Action in U.S. Appl. No. 15/152,411, dated Dec. 7, 2016, 10 pages.

Non-Final Office Action in U.S. Appl. No. 15/279,845, dated Apr. 21, 2017, 10 pages.

Non-Final Office Action in U.S. Appl. No. 15/337,222, dated Mar. 23, 2017, 13 pages.

Non-Final Office Action in U.S. Appl. No. 15/382,126, dated Mar. 17, 2017, 16 pages.

Non-Final Office Action in U.S. Appl. No. 17/146,473, dated Mar. 19, 2021, 33 pages.

Non-Final Office Action in U.S. Appl. No. 16/800,952, dated Sep. 1, 2020, 17 pages.

Notice of Allowance in U.S. Appl. No. 17/163,336, dated Aug. 5, 2021, 26 pages.

Obgyn.com [online], "Neural Networks", 2002, retrieved on Jan. 19, 2021, retrieved from URL<http://www.obgyn.cam.ac.uk/cam-only/statsbook/stneunet.html>, 34 pages.

Rabelo et al., "Development of a real-time learning scheduler using reinforcement learning concepts," Presented at 9th IEEE International Symposium on Intelligent Control, Aug. 16-18, 1994, pp. 291-296.

Notice of Allowance in U.S. Appl. No. 17/146,473, dated Apr. 6, 2022, 14 pages.

* cited by examiner

MATCHING PATIENTS WITH DECENTRALIZED CLINICAL TRIALS TO IMPROVE ENGAGEMENT AND RETENTION

CROSS-REFERENCE TO RELATED APPLICATIONS

This application is a continuation of U.S. application Ser. No. 17/163,336, filed Jan. 29, 2021, now allowed, the entirety of which is incorporated by reference.

BACKGROUND

Many networked systems interact with large numbers of devices that have different contexts, capabilities, and users. Because of the large variety of endpoint devices that a system may interact with, not all of the same software, web pages, and content are compatible with or even useful for different devices. For most day-to-day interactions, such as streaming a video or loading a web page, the impact is small in magnitude and short in duration, for the server as well as the client device and its user. In these common interactions, there is an interaction between devices without a significant commitment of future resources by the client or server. The amount of computing resources expended is small and only of a brief duration, so that if the interaction is ended, e.g., a user stops a video or the user does not click on search results, the exchange has resulted in a very limited consumption of computing resources.

However, when remotely configuring devices or enrolling them in ongoing monitoring programs, applying an incorrect configuration or carrying out excessive monitoring can have a high impact. Enrolling a device in a monitoring program can often involve changes to the configuration of a device, causing the device to perform ongoing or repeated monitoring actions over days, weeks, or months. These actions can significantly affect the performance and usability of a device, by affecting battery life, network bandwidth usage, data storage, processor utilization, and so on. It is important that monitoring programs and their configuration changes are distributed where the monitoring will be appropriate and effective, to avoid wasting limited resources of endpoint devices such as phones, smartwatches, tablet computers, and so on. In addition, in many cases server systems and other systems may rely on the data collected from devices enrolled in monitoring programs, and may be ineffective at completing their monitoring objectives if client devices do not carry out monitoring as required. Similarly, when client devices provide incomplete, inaccurate, or monitoring data this can result in significant costs to servers in terms of power consumption, network bandwidth usage, data storage, and other resources for data collection and processing that does not achieve the monitoring objective.

SUMMARY

In some implementations, a computer system provides a platform for publishing and distributing configuration data to involve different remote devices in various monitoring programs. The system enables different parties, e.g., organizations, administrators, third-parties, etc., to create or register monitoring programs to be distributed and managed by the system. The system uses various techniques, including machine learning models and various types of profiles, to selectively determine which monitoring programs, if any, are appropriate for different remote devices. The processing involves analysis of factors such as characteristics of the remote devices and their users, the requirements and objectives of the monitoring programs, and predictions regarding the outcomes of enrolling users and their devices in specific monitoring programs (e.g., likelihoods of completion of the program, retention in the program, achieving desired levels of data quality or data collection completeness, etc.).

The system uses various information about monitoring programs, devices, users, and historical outcomes to identify and provide a customized set of monitoring programs for each candidate device or user. The set of monitoring programs can also be adaptively changed and adjusted as circumstances change, for example, as the context of a user or device changes, as more information about the user or device is received, or as the enrollment of different monitoring programs rises or falls. The analysis by the system can identify customized sets of candidate monitoring programs for different remote devices, which can greatly improve the efficiency with which the system distributes and conducts monitoring with remote devices. The system identifies and distributes the programs that are most compatible with and beneficial to a device and its user and/or those which are predicted to be most likely to be carried out according to the requirements of the monitoring program. This selective distribution helps ensure that resources are focused on the limited set of monitoring programs that will provide useful results and the requirements of the programs will be met (e.g., the monitoring can be carried out in the appropriate manner and for the full duration needed). The system filters out or avoids providing monitoring programs to a device when the system determines that monitoring program would represent a waste of computing resources if initiated, such as where the program has a low likelihood of being completed successfully for the device or user, or where the data that would be collected would be unnecessary (e.g., redundant with existing monitoring of other similarly-situated devices) or would be of low quality.

As a result, unlike many systems that seek to maximize the number of devices involved in monitoring regardless of the predicted effectiveness, the system can tailor the monitoring program options for each device or user, limiting the monitoring programs that are distributed to and initiated by specific devices to the programs for which monitoring is most likely to be completed effectively and for which the results will be valuable and useful. This conserves resources for both client devices and servers by avoiding the distribution and running of monitoring programs that are redundant, ineffective, or unlikely to be carried out correctly.

Systems that manage and distribute monitoring programs over the Internet commonly encounter the problem of poor responsiveness and poor reliability among the devices that receive and begin monitoring programs. Frequently, from the set of devices that begin a monitoring program, the percentage of devices that reliably perform monitoring and report the needed data back to the server is much lower than needed. This often represents significant wasted resources, since partial data or low-precision data often fails to meet the needs of a monitoring scheme—the data often needs to be discarded and the resources consumed (both for work done previously and for monitoring on an ongoing basis) is wasted. In many monitoring programs, especially where users may opt-in or opt-out, there are many devices that begin a monitoring program and do not continue for the full duration needed to meet the objective of the monitoring program. This represents a significant inefficiency, where devices may be consuming power, network bandwidth, processor utilization, and storage space on an ongoing basis even when the data collected is incomplete and will not achieve the objective of the monitoring.

The present system conserves resources and improves the rate at which devices carry out monitoring programs by intelligently selecting which monitoring programs are appropriate for different devices, users, and contexts. This includes using information about characteristics of devices, users, and monitoring programs, as well as historical information about compliance with monitoring programs, to predict how well different user and devices will comply with the needs of different monitoring programs. the system can train and use machine learning models to determine these predictions. With the predicted compliance and retention information, the system can distribute and initiate monitoring programs where they are most likely to be effectively performed and avoid enrolling devices that will not likely comply with the requirements of the monitoring program. For example, one monitoring program may require hourly updates with sensor measurements over a period of three months. The system can generate models of how different devices and users in different contexts have interacted and provided data in this monitoring program and other monitoring programs. With the models, the system can weight or prioritize the recommendation of and distribution of the monitoring program for devices, users, and contexts having characteristics similar to those that have resulted in effective compliance with the sensor data collection, hourly reporting, and 3-month duration of the program. Conversely, for devices, users, and contexts where monitoring has not been successful for one or more of the needed program elements, the system can demote or avoid providing the monitoring program to avoid incurring unnecessary, inefficient resource usage to initiate and continue monitoring that is unlikely to be completed properly.

Systems that manage and distribute monitoring programs over the Internet also commonly encounter the problem of failing to distribute monitoring programs widely enough to meet the objectives of the monitoring programs and in a sufficiently targeted manner to monitor the right types of devices and users. Often, a monitoring scheme has an objective that requires a minimum number of devices in varying contexts in order for the data to be reliable and representative for a population. Many monitoring programs also need devices and users with specific contexts or characteristics in order to be effective, which limits the available pool of candidates and makes the automated recruitment of monitored subject more challenging. For example, some monitoring programs may require measurements using a specific combination of sensors or a specific level of accuracy that limits which devices can be used. Similarly, some monitoring programs may be tailored to monitor specific events, conditions, or situations and so devices and users having specific contexts and backgrounds are needed. Many distribution systems, such as typical application stores and content distribution networks, are unable to assess the suitability of different devices and users for different monitoring programs or ineffective at it, leading them to recommend and distribute programs to devices where the programs are incompatible, redundant, ineffective to achieve monitoring objectives, or are unlikely to be used successfully.

The systems discussed herein are able to more effectively recruit the numbers and types of devices and users needed for various monitoring programs, and to target the recruitment to devices and users most likely to perform the needed types of monitoring for the duration of the monitoring program. The system can use information about the needs of the different monitoring programs, including the numbers of devices and users to monitor for each monitoring program, as well as the attributes, contexts, history, and other factors that are needed to make a candidate a good fit for a monitoring program. For example, the system can select and rank monitoring programs for a device or user taking into account the total number of monitored subjects the monitoring program needs, the current level of enrollment relative to the needed total, the factors (e.g., monitored subject attributes) for each monitoring program that make subjects more or less valuable to achieving the objectives of each monitoring program, and so on. The analysis by the system can identify, from among a large pool of candidates, which candidates provide the most valuable data (e.g., due to the subject's context, attributes, history, etc.) and the most likelihood, allowing the system to better fill each monitoring program with the number of subjects needed and with the types of subjects needed. In some implementations, this results in customized recommendations of monitoring programs to different devices or users, each being selectively provided a set of monitoring programs dynamically and adaptively determined to optimize the criteria for value of the collected data to the researcher or program administrator and value of the monitoring to the subject, while accounting for the likelihood of compliance and retention in the program and limits for the burden placed on devices and users (e.g., actively accounting for the resource consumption a program places on devices and the time commitments required of users to participate in a monitoring program).

Unlike many distribution platforms, the present system can balance the needs of different monitoring programs from among a pool of limited candidates. While many different organizations may desire to conduct monitoring through the system, there is often a limited pool of devices and users that can participate, and each device or user may be limited to participating in a small number of the monitoring programs available to avoid overburdening individual devices or users. Monitoring programs are not compatible with every device or user, and some programs are more strict in their requirements than others. Users appropriately have control their own devices and should select which monitoring programs to participate in, but may not understand which of many (e.g., often hundreds or thousands) monitoring programs are best suited for their devices, habits, and needs, or which monitoring programs their participation in would yield the greatest value. The system discussed herein, however, can account for these factors in the manner in which it selects, ranks, and prioritizes monitoring programs for different remote devices and their users, to allocate the limited opportunities available for monitoring programs to be carried out by candidates among the many monitoring programs to be carried out. This helps tailor the monitoring program options presented for each device and user to those that are appropriate for and valuable to the device and user, while also enabling the system to recruit the needed numbers and types of devices and users that monitoring programs need to meet their overall objectives for aggregating data from many devices and users.

The system can facilitate remote configuration of the sensors, user interfaces, network communication settings, and other aspects of remote devices so that monitoring programs are started and continued by the remote devices. By selectively involving remote devices in monitoring programs predicted by models to have the highest likelihood of success, the system can achieve monitoring with much higher efficiency, effectively reducing the consumption of resources of monitoring that will be only partial, of too short of a duration, or with unacceptable data quality.

In some implementations, the monitoring programs can be used for scientific research or health research. The systems and techniques herein can use machine learning models to select and recommend monitoring program opportunities that are likely to satisfy the needs and preferences of a potential participant in a program as well as the research requirements associated with participation in the program. As described throughout, programs can represent research studies that users can choose to participate in and initiate monitoring using their electronic devices, with the software modules and device configuration needed being distributed through an Internet-based software platform. Researchers use the software platform to design research studies and allow users of the software platform to participate in the research studies. The software platform may provide program opportunities when, for example, a user is interested in participating in one or more programs that are seeking enrollment of additional participants.

For example, the system can identify a research study for which (i) a user's participation is likely to be beneficial to the user and (ii) the user's participation is also likely to benefit one or more research objectives of a researcher that conducts the study. In this way, the predictions generated by the system can be applied to align the requirements of participants and researchers, thereby increasing the likelihood that user participation will be mutually beneficial to the user and the researcher.

The system can provide customized predictions that improve the alignment of user interests, needs or preferences, and research outcomes. For example, the system can evaluate the attributes of different users and their level of compliance with different monitoring program requirements (e.g., types of data collected, frequency of data collection, duration of participation, consistency, activities needed, etc.). With the analysis results or a machine learning model trained based on the data, the system can predict how the probability and level of compliance of other users with specific requirements of a monitoring program or for total set of requirements of the monitoring program. Using these models, and by evaluating a user's historical study participation data in relation to research requirements related to participant compliance, the system can predict how likely a user is to successfully complete the various requirements of different monitoring programs. The system can then use these predictions to rank and prioritize studies to recommend and distribute to each device and user, which can avoid many of the inefficiencies and ineffective monitoring that result from monitoring programs that are initiated and not performed effectively.

For example, the system may identify a first monitoring program for a research study that aligns moderately with user's interests, where the user has a background making collected data useful to achieving the research study's objective, and where the predicted probability of user compliance in the research study is high. A second monitoring program may better align with the user's interests but have a lower predicted probability of compliance with that monitoring program's requirements. As a result, even though second monitoring program is better aligned to the user's preferences, the system prioritizes the first monitoring program that is less aligned to a user's preferences because the system's analysis indicates that the user is not likely to be compliant in the better-aligned program. Thus, the system guides the user to participate in a research study that still aligns with his/her interests but has a higher probability of compliance, which increases the probability of a successful study outcome (e.g., retention for the duration needed and compliance with study requirements).

The architecture of the system provides various technological improvements in predictively evaluating user data (e.g., user attributes, user preferences, user interaction data) and research requirement data (e.g., study design parameters) for a program in selectively generating recommendations for the program. Using different types of data, the system generates recommendations in a manner that improves the likelihood of a beneficial outcome for a user that is provided a recommendation to participate in a program and a researcher that manages the program. To accomplish this, the system processes user data and research requirement data using learning models to identify program opportunities (e.g., identifying a program that a specific user is likely to benefit from by participating in the program and for which the specific user's participation is likely to satisfy one or more research requirements of the program). The system can apply the learning models on an ongoing basis so that recommendations accurately represent any changes in program availability, user preferences, research requirements, among other factors.

In one general aspect, a method performed by one or more computers, the method comprising: accessing, by the one or more computers, a candidate profile for a candidate to participate in interactive programs involving collection of data from participants using remote devices and reporting of the collected data over a communication network, the candidate profile describing attributes of the candidate; identifying, by the one or more computers, program profiles for multiple programs in which the candidate is eligible to enroll as a participant, wherein the program profiles (i) describe the respective programs and (ii) indicate types of data to be collected in the respective programs; determining, by the one or more computers, one or more scores for each of the programs with respect to the candidate, wherein the one or more scores for each program are based on: (i) a relevance of the program to the candidate determined based on the attributes of the candidate as indicated by the candidate profile; and (ii) a predicted level of compliance of the candidate in providing the types of data to be collected in the program, wherein the predicted level of compliance is based on the attributes of the participant; selecting, by the one or more computers, one or more of the programs based on the scores for the programs; and providing, by the one or more computers, selection results over the communication network to a client device associated with the candidate, the selection results being provided for presentation by the client device to indicate the selected one or more programs on an interface of the client device.

In some implementations, the method includes: selecting, by the one or more computers, a configuration data package corresponding to a particular monitoring program indicated by the selection results; and delivering, by the one or more computers, the configuration data package to the client device associated with the candidate, the configuration data package including one or more settings to adjust a configuration of the client device to initiate monitoring by the client device according to the particular monitoring program.

In some implementations, the configuration data package comprises configuration data configured to adjust operation of one or more sensors of the client device to perform a series of measurements to collect, at the client device, one or more types of data specified by the monitoring program.

In some implementations, the configuration data package is configured to adjust communication of the client device to receive measurement data from a second device over a wired or wireless interface and to report the measurement data to the one or more computers over the communication network.

In some implementations, the one or more computers are part of a distribution platform configured to (i) selectively provide monitoring programs to remote devices of users registered with the distribution platform, the monitoring programs including monitoring designed by different third-party organizations, and (ii) receive, process, and store data for the respective monitoring programs from the remote devices and provide aggregated data for each of the monitoring programs to the respective third-party organizations corresponding to the monitoring programs.

In some implementations, the candidate profile indicates interests of the candidate; the program profiles describe the topics or subjects of the programs; and the scores are based on a level of similarity of the interests of the candidate indicated by the profile to the respective topics or subject of the programs as indicated in the program profiles.

In some implementations, the method includes determining a preferred level of interaction of the candidate; and determining that the participant actions for a particular program exceed the preferred level of interaction of the candidate. Determining the scores comprises applying a penalty to a score for the particular program based on determining that the participant actions for a particular program exceed the preferred level of interaction of the candidate.

In some implementations, the method includes determining, for each of the programs and based on the attributes of the candidate indicated in the candidate profile for the candidate, a predicted likelihood of compliance or predicted level of compliance of the candidate in performing the participant actions for the programs. The scores are based on the predicted likelihoods of compliance or predicted levels of compliance.

In some implementations, the predicted likelihood of compliance or predicted level of compliance is generated by providing information indicating the attributes of the candidate to a machine learning model trained based on the attributes of other individuals and actions of the other individuals while enrolled in one or more programs as participants.

In some implementations, the programs include clinical treatment programs.

In some implementations, the programs correspond to different health research studies.

In some implementations, the programs are research studies that each have cohort inclusion criteria or cohort exclusion criteria. The method comprises determining whether the candidate is eligible to participate each of the research studies based on whether the user satisfies cohort inclusion criteria for the respective research studies or whether the user satisfies cohort exclusion criteria for the respective studies. The multiple studies are identified by filtering a set of programs to identify a subset of the programs for which the candidate is determined to be eligible.

In some implementations, determining the scores comprises: assessing a composition of sets of participants enrolled in the respective programs; determining that the candidate has one or more attributes that are underrepresented in the set of participants for a particular program; and weighting one or more scores for the candidate for the particular program based on determining that the candidate has one or more attributes that are underrepresented in the set of participants for a particular program.

In some implementations, program profiles indicate participant actions that participants are requested to perform as part of participation in the respective programs.

In some implementations, the one or more scores for each program are determined based on a level of compatibility between participant actions of the program and a level of engagement preferred to be predicted for the candidate.

The details of one or more implementations are set forth in the accompanying drawings and the description below. Other potential features and advantages will become apparent from the description, the drawings, and the claims.

BRIEF DESCRIPTION OF THE DRAWINGS

In the drawings, like reference numbers represent corresponding parts throughout.

DETAILED DESCRIPTION

This disclosure describes systems and techniques for using learning models predict program opportunities that are likely to satisfy user's participation needs for a program and research requirements associated with user participation in the program. For example, using these predictions, a system can identify a research study for which (i) a user's participation is likely to be beneficial to the user and (ii) the user's participation is also likely to benefit one or more research objectives of a researcher that conducts the study. In this way, the predictions generated by the system can be applied to align the requirements of participants and researchers, thereby increasing the likelihood that user participation will be mutually beneficial to the user and the researcher.

Figure 1A:
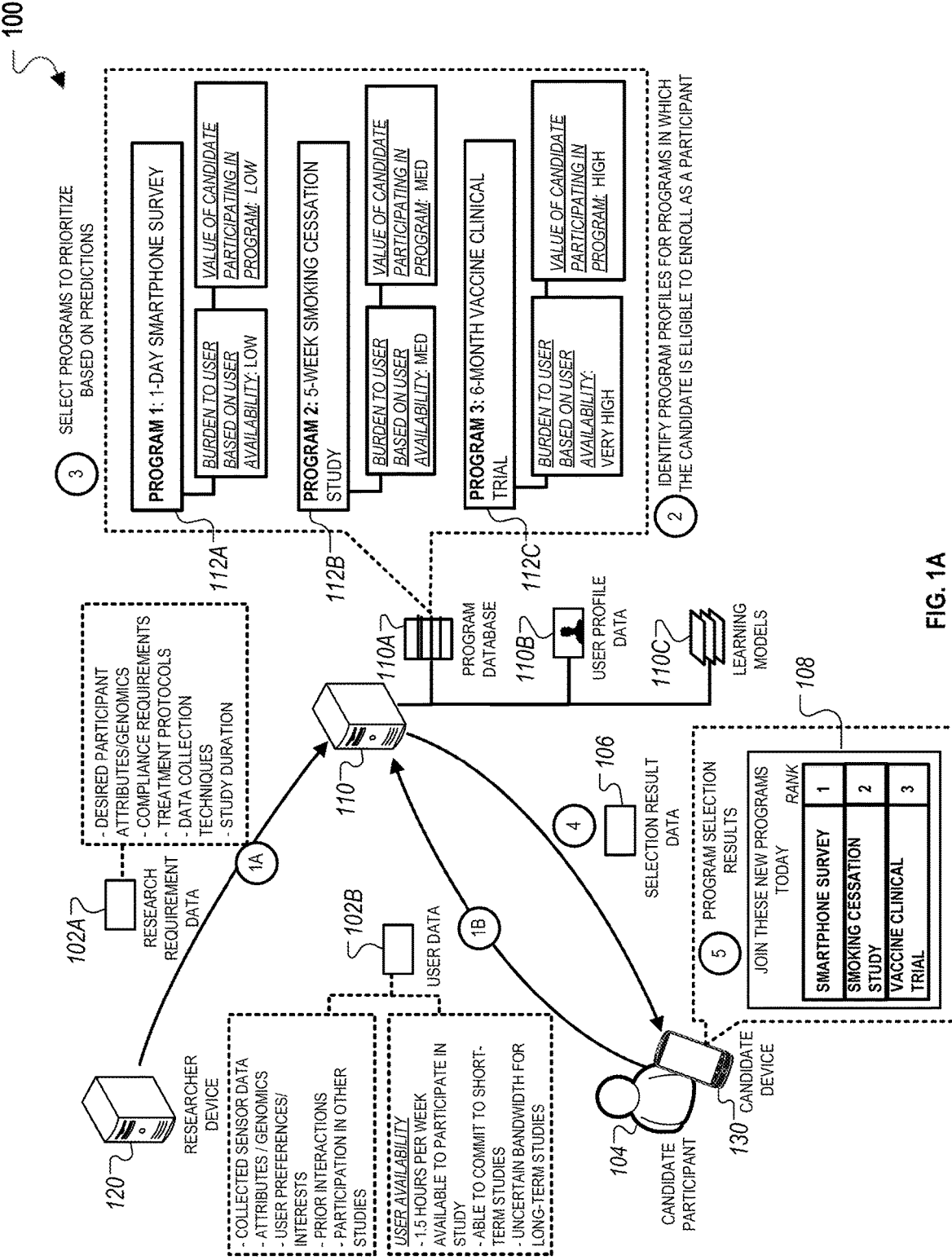
FIG. 1A illustrates an example of a technique for prioritizing programs opportunities within a software platform based on user data and research data.

FIG. 1A illustrates an example of a technique for predicting programs opportunities within a software platform based on user data and research data. The software platform is provided by a system 100 including a server 110, a device 120, and a device 130. The server 110 provides various services related to the software platform, such as enabling researchers to design programs, publishing programs designed by researchers through the software platform, and enabling computing devices to allow users (e.g., participants of research studies) to access and participate in the programs. Device 120 is a computing device of a researcher that designs programs (e.g., research studies) available through the software platform. Device 130 is a computing device of a user 104 that accesses programs available on the software platform through, for example, a mobile application that runs on the device 130 or a webpage accessed through a web browser.

As described throughout, a "program" refers to an interactive software program that typically involves user interaction, such as inputting information, modifying information, managing information, or otherwise manipulating data. Programs can be created by communities of program administrators and deployed through a software platform provided by the server 110. Program administrators can include researchers, coaches, healthcare providers (e.g., physicians), among others. Programs can relate to research studies managed by program administrators, therapeutics and performance-related engagements, among other types of interactive user experiences.

Programs can also contain varying data sets based on data collection needs from survey instruments, passive sensors, wearable devices, electronic health record (EHR) software, genomics, bio-sample data, and other types of healthcare data (e.g., demographics, medical history, family history), or interaction data collected on computing devices (e.g., behavioral data, environment data, lifestyle data). Construction of a program can be based on opportunities provided to both a program administrator and users of the software platform. For example, when conducting a research study, a program administrator may have specific research objectives, such as observing hypertension in an adolescent age segmentation. In this example, if a user falls within the adolescent age segmentation and has been diagnosed with hypertension, then the user's participation in the research study may be determined to mutually benefit both the program administrator and the user.

Referring back to FIG. 1A, the server 110 includes a program database 110A storing a list of programs available through the software platform (including programs for which program opportunities are identified). The server 110 stores a user profile 110B identifying preferences of the user 104. As discussed below, the server 110 also includes one or more learning models 110C that are trained to identify and select programs to prioritize for suggesting to the user 104.

The user profile 110B includes various types of user information that can be adjusted over time to reflect changes in user's condition (e.g., health condition), user preferences (e.g., motivations or objectives in participating in programs), user interaction behaviors (e.g., how the user accesses device 130 in interacting with programs), among others. The user profile 110B is generated after an initial registration when the user 104 joins or opts into the software platform. During initial registration, the user 104 can complete an initial assessment and provide input related to registration-related data fields. Such fields can include demographic information (e.g., age, ethnicity, race, gender), medical history information (e.g., pre-existing conditions, intake encounter information from EHR software), and family history (e.g., conditions, disease-related risks, family origins). Other fields include lifestyles information (e.g., exercise, smoking, alcohol use, drug use, extravert, introvert, social network, environmental information (e.g., air quality, mineral deposit, lead in the water), device information (e.g., smartwatch, trackers, monitors, assessment tool reports), claim data (e.g., encounters, frequency, medications), clinical data (e.g., bio-sample data, test results), genetic analysis (e.g., gene variants) and microbiome data.

The program prioritization technique shown in FIG. 1A proceeds in a set of steps. At step 1A, server 110 receives research requirement data 102A from the device 120. As shown, the research requirement data 102A includes features specified by a researcher for a research study. The research requirement data 102A can include desired participant attributes or genomics, such as demographic profile, diagnosed conditions, physiological features, behavioral attributes). The research requirement data 102A can also specify compliance requirements for the research study, which refers to the extent patient behaviors during a study can deviate from treatment protocols and still represent validly collected experimental data. As another example, the research requirement data 102A can specify treatment protocols, such as surveys to be completed during the research study, procedures to be completed by patients, or prescriptions to be taken by users while participating in the research study. Additionally, the research requirement data 102A can specify data collection (e.g., type of data to be collected, frequency of data collection) and study duration (e.g., one-day study, one-week study, one-month study, etc.).

At step 1B, the server 110 receives user data 102B from the device 130. As shown, the user data 102B includes various types of information associated with the user 104. For example, the user data 102B can include sensor data collected by the device 103 and/or a companion wearable device that may be used by the user 104 (e.g., heart rate data, pedometer data, accelerometer data, global positioning sensor (GPS) data, etc.). The user data 102B can also include passively sensed data that detected or identified, such as context data, interaction data, cursor movement data, among others. The user data 102B can further specify user attributes or genomics data, such as demographic information, previously diagnosed conditions, physiological attributes, phenotypical information, or medications currently being taken by the user. Additionally, the user data 102B can include interaction data (e.g., data indicating how and when the user 104 interacts with graphical user interfaces provided on the device 130), and study participation data (e.g., research studies that the user 104 previously participated in or compliance or retention information associated with the research studies).

At step 2, the server 110 predicts program opportunities based on applying the learning models 110C to the research requirement data 102A and the user data 102B. As described throughout, a program opportunity represents an option for a user to enroll in a program through the software platform. For example, a user may have recently completed a program and is now interested in participating in a new program. In other examples, where users can participate in multiple programs during the same time period, a program opportunity may represent a user looking to enroll in a program based on his/her interests or needs.

The server 110 predicts program opportunities by providing the research requirement data 102A and/or the user data 102B as input to the learning models 110C and obtaining, as output from the learning models, data indicating one or more programs included in the program database 110A that are likely to be beneficial to the user 104 (based on information specified in the user data 102B) and also satisfies certain requirements specified in the research requirement data 102A.

The learning models 110C can be, for example, machine learning models that are trained using training datasets of other users of the software platform and research requirement data for known research studies that were previously completed. The training datasets can specify features indicating user interests in programs, which allow the learning models 110C to predict programs that are likely to be of interests for the user 104. For example, the training datasets may specify associations between a set of user attributes and the types of programs that users having one or more of the set of attributes previously enrolled. In this example, the learning models 110C may use pattern recognition based on the attributes of the user 104 and the set of attributes to predict the programs that a user 104 is likely to find beneficial based on his/her attributes.

As another example, the learning models 110C may also be trained to use user behavioral information as indicators to predict whether a user will be satisfied with enrollment in a particular program. In this example, the learning models 110C may use known patterns between historical behaviors of other users and enrollment outcome data indicating whether users found their participation in a program to be beneficial or useful to his/her interests. In this way, the learning models 110C can predict, based on user behaviors specified in the user data 1028, whether the user 104 is likely to benefit from a particular program.

At step 3, the server 110 selects three programs 112A, 112B, and 112C from the program database 110A for prioritization based on the program opportunities predicted by the learning models 110C. In the example shown in FIG. 1A, the learning models 1100C predict that the programs 112A-112C may be beneficial to the user 104 based on the information specified by the research requirement data 102A and the user data 102B. As described throughout, the programs 112A-112C are identified not only because their subject matter aligns with interests of the user 104, but also because participation in the programs 112A-112C by user 104 may also be beneficial to a researcher of the device 120. In this sense, programs 112A-112C are identified as mutually benefitting both the user 104 and the researcher to a larger extent than other programs available for enrollment within the program database 110A.

As shown in FIG. 1A, each of the programs 112A-112C include certain program attributes that makes their selection useful for the predicted program opportunities. Program 112A is a one-day research study that involves a user completing a survey on a smartphone, which is predicted to have a low user burden (due to a short time commitment required from a user) but also have low research value (due to low quality of research data collected through the program). Program 112B is a five-week study studying the effects of user behaviors on smoking cessation, which is predicted to have a medium user burden (due to time commitment required from a user) and medium research value (due to the amount of data collected from users during the program). Program 112C is a six-month clinical trial for a potential vaccine, which is predicted to have a high user burden (due to the longevity of the study and the compliance required from the user) and high research value (due to the importance of research findings as the program outcome).

The server 110 selects programs 112A-112C from the program database 110A based on various factors indicating that they are useful for predicted program opportunities. For example, program 112A may be selected since the user data 1026 indicates that the user 104 has a smartphone, the user 104 is included within an age demographic that typically prefers quick and short surveys, and study participation data of the user 104 indicates that he/she has previously participated in similar programs. Program 112B may be selected since the user 104 is identified as a smoker and the user profile data 1106 indicates that he/she is interested in stopping a smoking habit. Finally, program 1122C may be selected since the research requirement data 102A indicates that vaccine development is an ongoing public heath priority that has significant research funding opportunities and since the cohort inclusion criteria for the vaccine trial includes genomic attributes that match the genomic attributes of user 104.

At step 4, the server 110 provides selection result data 106 to the device 130. The selection result data 106 identifies a ranking computed by the server 110 for each of programs 112A-112C based on the research requirement data 102A and the user data 1026. The rankings represent a relative prediction by the server 110 that (i) the user 104 will benefit from participation in the program (e.g., based on the user's interests and goals) and (ii) the user's participation will satisfy research requirements for the program and/or advance objectives of the program (e.g., whether the user is likely to complete the program, whether the user is likely to comply with treatment protocols, whether the user will perform certain actions that are beneficial or detrimental to research objectives, etc.).

In the example shown in FIG. 1A, selection result data 106 indicates that program 112B is ranked first, program 112A is ranked second, and program 112C is ranked third. As discussed above, these rankings reflect a prediction by the server 110 that the user's participation program 112B is most likely to mutually benefit the user 104 and the researcher. That is, the server 110 predicts that the user's participation in program 112B has the highest likelihood of providing user satisfaction based on the user data 1026 and satisfying the research requirement data 102A.

As shown in FIG. 1A, the rankings of programs 112A-112C are based on two distinct criteria—user burden (e.g., the amount of time required for a user to complete a program) and research value (e.g., a research priority amongst different programs actively seeking enrollment). In this example, program 112A has the highest ranking since the server 110 predicts that this program is most likely to be completed by user 104 while also generating productive research data. In contrast, while program 112A has the highest likelihood of completion due to low user commitment, the research data generated is not valuable to the researcher. Likewise, while program 112C has the greatest research value, the user data 104 indicates a very low likelihood that user 104 will successfully complete the program (which ultimately reduces the program outcome for the researcher and the participant).

At step 5, the device 130 provides an interface 108 through which a ranked list of prioritized programs is made available for viewing for the user 104. The interface 108 includes a ranked list of programs 112A-112C based on the rankings discussed above. Interface 108 can be presented through, for example, a program enrollment page of a mobile application for the software platform. The interface 108 can be displayed in response to user input indicating that the user 104 is seeking a program to enroll (e.g., by navigating to a program enrollment page of the application) or in response to passive detection of information indicating that a user may be looking for a new program to join (e.g., a user recently completing a program, a user performing a search query for programs, etc.).

As discussed throughout, various factors or dimensions can be used by the learning models 110C to determine programs that should be prioritized for a program opportunity. Examples of such factors include user preference or relevance of the subject of a program to user interests, preferences of a research in recruiting participants, or the value of a particular user enrolling in a research study. Other factors involve predictions relating to the user enrolling in a program, such as predicted compliance of the user while enrolled in the program, or prediction retention of the user's enrollment during the entirety of the program.

Some other factors relate to outcomes predicted to be produced as a consequence of program enrollment, such as a predicted quality of data to be collected from the user, or a burden placed on the user in participating in the program. User burden can be determined based on specificity or multiplicity of the requirements for a program (e.g., as specified by research requirement data). Additionally, or alternatively, user burden can be determined based on considering a user's availability for participating in a program. For example, if a user has two hours in every week to allocate towards participation and has used 1.5 hours committed one program, then the user burden can be adjusted to 0.5 hours per week.

In some implementations, in determining which programs to prioritize for a given program opportunity, the learning models 110C may be applied to consider how far along recruitment for the program has progressed. For example, if a program is in the early stages of recruitment, program criteria may be more strictly applied to only focus on users with attributes or interests that most likely to align with study interests and/or have previously exhibited behaviors that make them strong participants (e.g., high retention in prior enrolled programs, strong compliance record in previously completed programs). Alternatively, if recruitment for a program has taken longer than originally anticipated due to the lack of availability of best-suited candidates, then learning models 110C can be applied to use more relaxed program criteria and/or more relaxed application of program criteria to increase the number of users for which the program is prioritized.

Figure 1B:
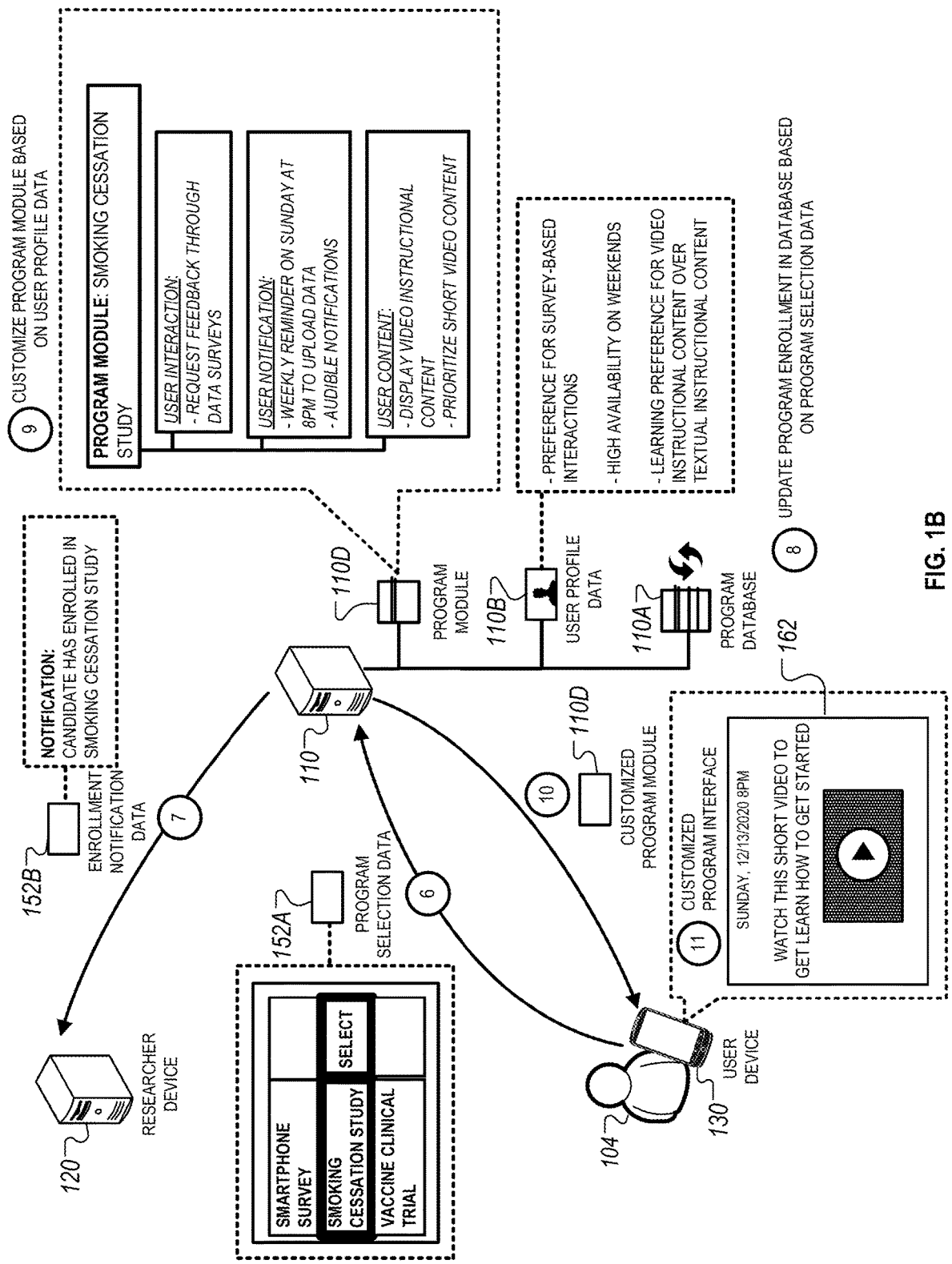
FIG. 1B illustrates an example of a technique for providing a customized program module to a client device of a user that selects a program for participation.

FIG. 1B illustrates an example of a technique for providing a customized program module to a client device of a user that selects a program for participation. The technique shown in FIG. 1B proceeds in a set of steps after the user 104 selects one of the programs that were selected by server 110 and indicated within the selection result data 106. At step 6, device 130 provides program selection data 152A to server 110. As shown, the user 104 selects the smoking cessation study from the interface 108 in step 5 (shown in FIG. 1A), which is indicated in the program selection data 152A.

At step 7, the server 110 provides enrollment notification data 152B to device 120. The enrollment notification data notifies a research that the user 104 has enrolled in the smoking cessation study. The researcher can decide at this stage to push information to the user, such as actions the user should perform in preparation for participating in the research study (e.g., determining a baseline cigarette intake prior to beginning the study). In some instances, the researcher may have the option to decline or accept the user's participation in the study. In such instances, the researcher input can be employed as secondary confirmation for user participation.

At step 8, the server 110 updates program enrollment information in the program database 110A based on the program selection data 152A. For example, the server 110 may update an existing participant roster for a program, generate a participant record for a database element for the program, among other types of updates, update an access/ privilege setting so that device 130 is provided with access to program content stored on the server 110, among others. In some instances, step 8 is optionally performed by server 110 in response to receiving the program selection data 152A. In such instances, program data stored in the program database 110A is automatically updated based on the user's program selection and the server 110 proceeds directly to step 8 to generate a customized program module.

At step 9, the server 110 generates a program module 110D based on the user profile data 110B. The program module 110D is customized for the user 104 and/or the device 130 and configured to improve user experience while participating in the program. In the example shown in FIG. 1B, the server 110 uses three settings to customize the manner by which the user interacts with the program to improve, for example, user engagement, user retention, or the likelihood of obtaining a successful outcome.

The server 110 customizes values for the module settings based on information specified in the user profile data 110B. For example, the server 110 adjusts the user interaction setting to configure the program module 110D to solicit feedback through user surveys based on the user profile data 110B indicating that the user prefers providing feedback through surveys (as opposed to, for instance, providing feedback through a video conference with researchers). As another example, the server 110 configures the user notification setting so that the program module 110D is configured to provide weekly reminders for the user to upload study data each Sunday at 8 PM. In this example, the server 110 selects the notification settings based on high user availability on weekends and context data indicating that the user typically accesses device 130 during the evening time. The server 110 also selects the type of content and/or the manner in which the user interacts with the selected content. For instance, since the user profile data 110B indicates that the user 104 has a learning preference for video instructional content (as opposed to textual instructional content), the server 110 selects video content that is short enough (e.g., less than 5-minutes in duration) to maintain user engagement during playback.

At step 10, the server 110 provides the customized program module 110D to the device 130. At step 11, the server 110 generates a program interface 162 based on the configuration settings specified by the customized program module 110D. As discussed throughout, the customized program interface 162 can adjust the type of content provided to the user while participating in the research study, the arrangement of content provided, or the prioritization amongst different types of content to be provided. The customized program module 110D can also adjust how the content is provided through the program interface 162 (e.g., frequency of content being displayed, the times when content is displayed, or triggers/conditions that are required to be satisfied for providing content). Additionally, the content program module 110D can adjust the manner in which the user 104 interacts with the content provided through the program interface 162 (e.g., the types of user input that are used to interact with displayed content, user interface elements that are provided to allow user engagement, among others).

Figure 2A:
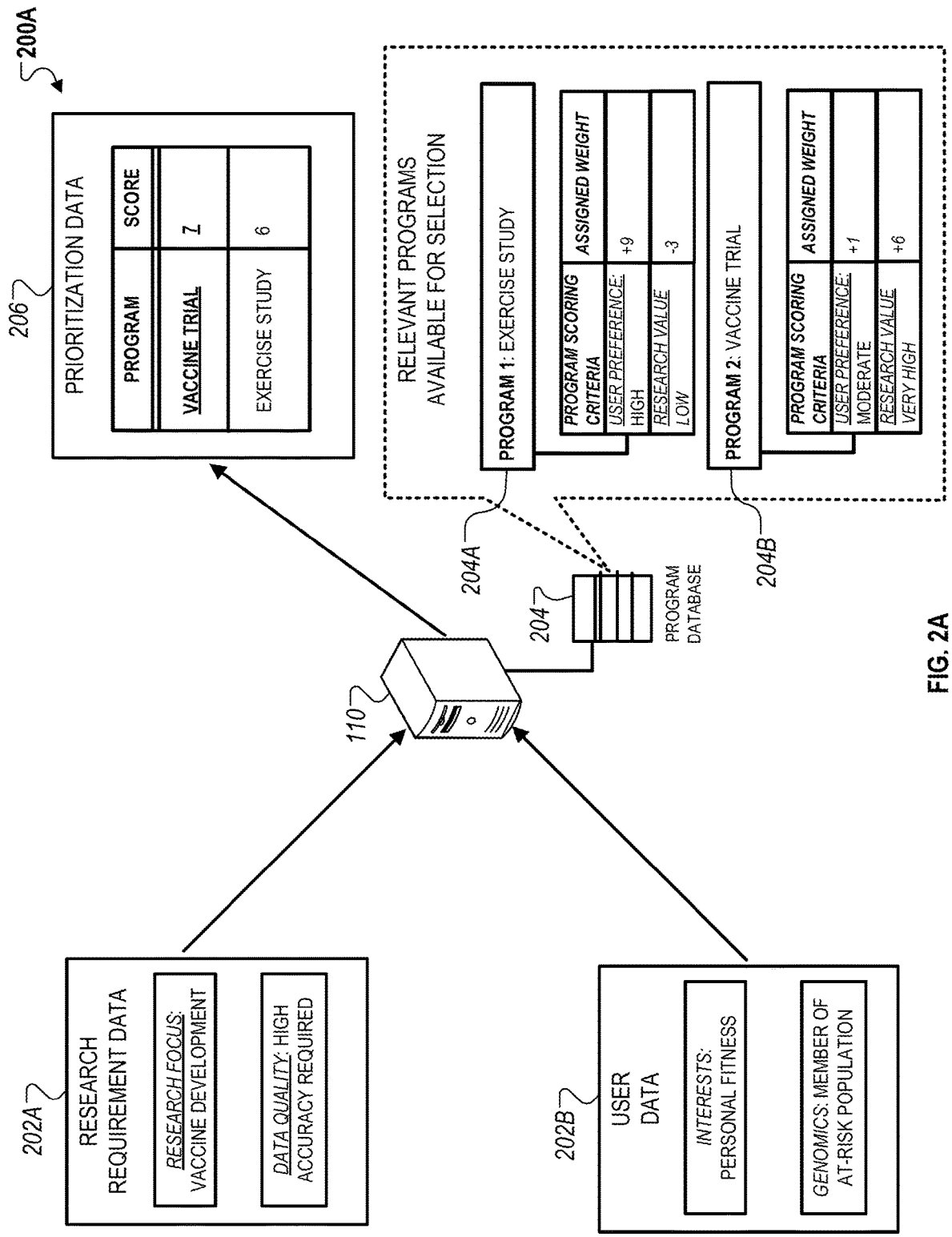
FIGS. 2A and 2B illustrate examples of techniques for prioritizing program opportunities based on evaluating program scoring criteria.
Figure 2B:
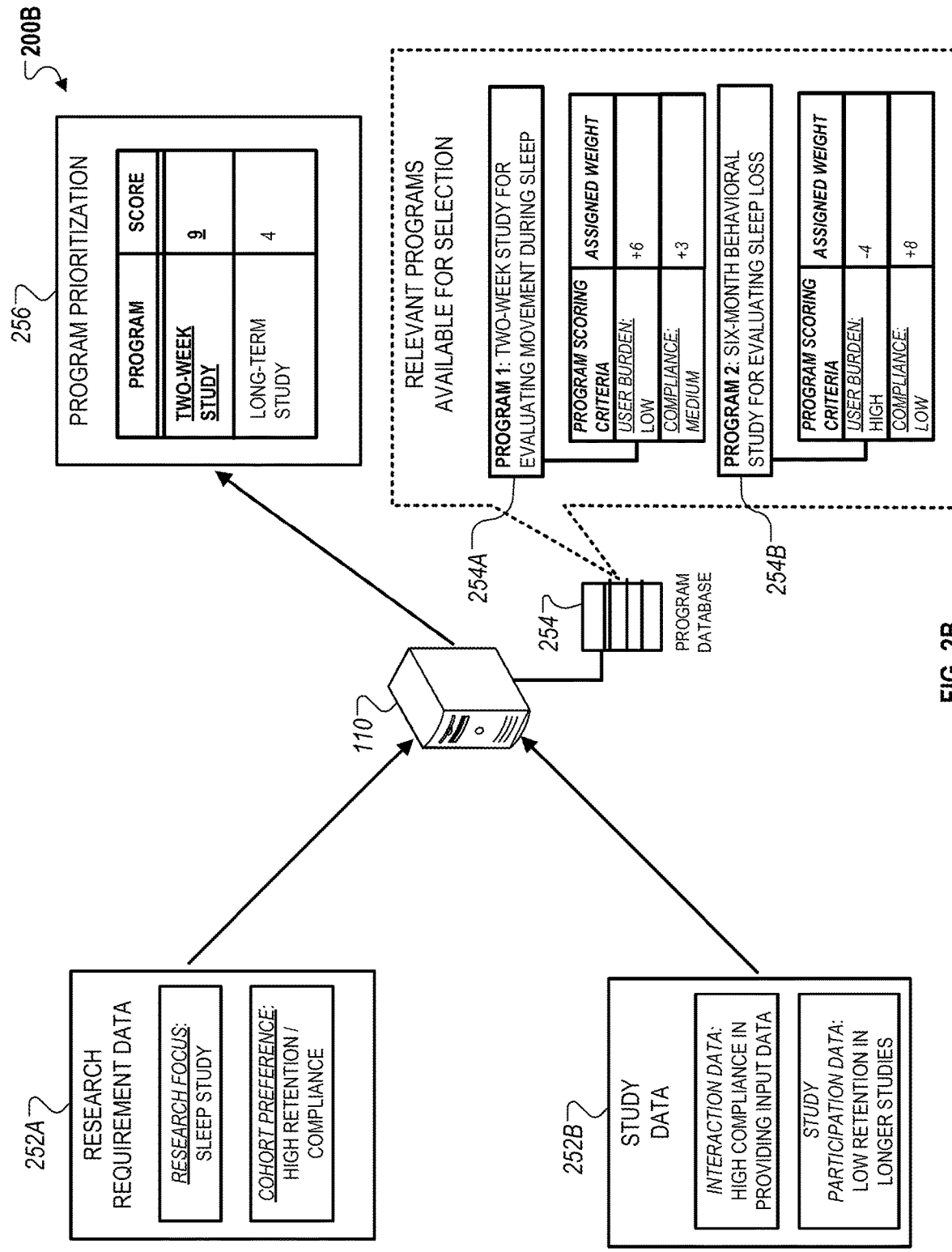

FIGS. 2A and 2B illustrate examples of techniques 200A and 200B for prioritizing program opportunities based on using weights to evaluate program scoring criteria. Referring initially to FIG. 2A, a technique for prioritizing program opportunities based on two program scoring criteria relating to user preference and research value is shown. In this example, user data 202B indicates that the user is interesting in improving his/her personal fitness and genomic data indicating that he/she is part of an at-risk population for an infection to be addressed by a vaccine being investigated by researchers. For example, the genomic data indicates that the user is a geriatric patient (e.g., older than old) with a respiratory disease, which makes him/her at-risk for contracting severe symptoms for COVID-19.

In the example shown in FIG. 2A, server 110 predicts program opportunities for programs included in program database 204 by initially identifying relevant programs available for selection. As shown, the server 110 identifies programs 204A and program 204B as being available for enrollment and being relevant to the research requirement data 202A and the user data 202B. For example, program 204A is an exercise study, which is related to the user's interest in personal fitness. Program 204B is a vaccine trial, which is related to the research objective of vaccine development.

Server 110 ranks each of programs 204A and 204B based on evaluating two program criteria (user preference and research value). The server 110 evaluates the program criteria by assigning weights to each program criteria based on predicting how likely program enrollment by a user is to satisfy a corresponding program criteria. For example, because the subject matter of program 204A strongly aligns with user motivation to improve personal fitness, the server 110 positively biases weighting using a value of "+9" for the user preference criteria. However, given that exercise data generated by the user's participation in program 204A is not related to vaccine development, the server 110 negatively biases weighting using a value of "−3."

For the second example, though the subject matter of program 204B is not perfectly aligned with his/her main interests, a user profile may indicate that the user has previously participated in clinical research studies. The server 110 therefore applies a slight positive bias for the user preference criteria using a value of "+1" since the user's study participation data indicates a possibility that the user may be interested in participating in a vaccine trial. Additionally, the server 110 applies a positive bias to the research value criteria using a value of "+6" since the research requirement data 202A indicates a prioritization for vaccine development.

The server 110 generates prioritization data 206 including scores computed based on the assignment of weights to the program criteria of each program. The value of a score, in this example, is computed based on combining the weights assigned for program criteria for each program. The scores thereby represent an evaluation of a user's participation in a corresponding program both satisfying the user's needs/preferences in program participation and requirements specified by the research requirement data. For example, the value for the score computed for program 204B is "7," which is higher than the value for the score computed for program 204A of "6." This is because the server 110 determines that user's participation in program 202B provides a stronger mutual benefit to the user and the researcher. In this example, program prioritization is focused on research value so that a program that is less focused on a user's preferences/needs is prioritized to the user (though it is still factored in the evaluation of prioritization).

In some implementations, scores indicated by the prioritization data 206 can represent predicted likelihood that user participation in a program will result in at least one beneficial user outcome (e.g., completing a user goal or objective) and at least one beneficial research outcome (e.g., retention of user participation that results in completion of a research study). In this example, the scores represent predictions that are collectively based on two types of inputs (research requirement data, user data) to trained learning models. A program for which a higher score is computed thereby represents a higher likelihood that the beneficial user outcome and the beneficial research outcome will be achieved based on the user's participation for the study.

Referring now to FIG. 2B, a technique for prioritizing program opportunities based on two program scoring criteria relating to user burden and compliance is shown. In this example, research requirement data 252A specifies a research focus criterion for a sleep study and a cohort preference criterion for high retention and/or compliance for participants enrolled in the sleep study.

User data 252B includes interaction data indicating that the user has previously had high compliance in providing input data when instructed to do so. For example, the interaction data indicates that the user has typically performed actions when requested to do so through a user interface of a mobile application. User data 252B also includes study participation data indicating that the user has low retention in longer studies. For example, the user may have dropped out of previously enrolled research studies that are longer than three-weeks long, resulting in a low retention record.

In the example shown in FIG. 2B, server 110 predicts program opportunities for programs included in program database 254 by initially identifying relevant programs available for selection. As shown, the server 110 identifies programs 254A and program 254B as being available for enrollment and being relevant to the research requirement data 252A and the user data 252B. For example, programs 254A and 254B are identified since they are both relevant to the sleep study research focus specified in the research requirement data 252A.

Server 110 ranks each of programs 254A and 254B based on evaluating two program criteria (user burden and compliance). Like the example shown in FIG. 2A, the server 110 evaluates the program criteria by assigning weights based on predicting how likely program enrollment is to satisfy a corresponding program criteria. For example, because the short (i.e., two-week) duration of program 204A creates a low user burden given the user's study participation data, the server 110 positively biases weighting using a value of "+6" for the user burden criteria. Additionally, given that the user's interaction data indicates high compliance in providing input data, the server 110 positively biases weighting using a value of "+3" for the compliance criteria.

For the second example, the server 110 applies a strong negative bias for the user burden criteria given the long (e.g., six-month) duration of program 204B, which creates a high user burden given that the user's study participation indicates that he/she has low retention in longer-term studies. The server 110 therefore negatively biases weighting using a value of "−4" for the user burden criteria. Additionally, given that the user's interaction data indicates high compliance in providing input data, the server 110 applies a strong positive bias to the compliance criteria using a value of "+8" for the compliance criteria.

The server 110 generates prioritization data 256 including scores computed based on the assignment of weights to the program criteria of each program. Like the example shown in FIG. 2A, the value of a score is computed based on combining the weights assigned for program criteria for each program. For example, the value for the score computed for program 254A is "9," which is higher than the value for the score computed for program 254A of "4." This is because the server 110 determines that, while program 254B may provide higher quality research data, the user is unlikely to complete this program given his/her study participation data. Program 254B there is less likely compared to program 254A in satisfying the cohort preference in seeking high retention and compliance. Instead, the server 110 opts to prioritize program 254A, which provides lower-quality research data but is still related to research focus and has attributes suggesting that the user will complete the program (and thereby satisfy the cohort preference for high retention).

Figure 3:
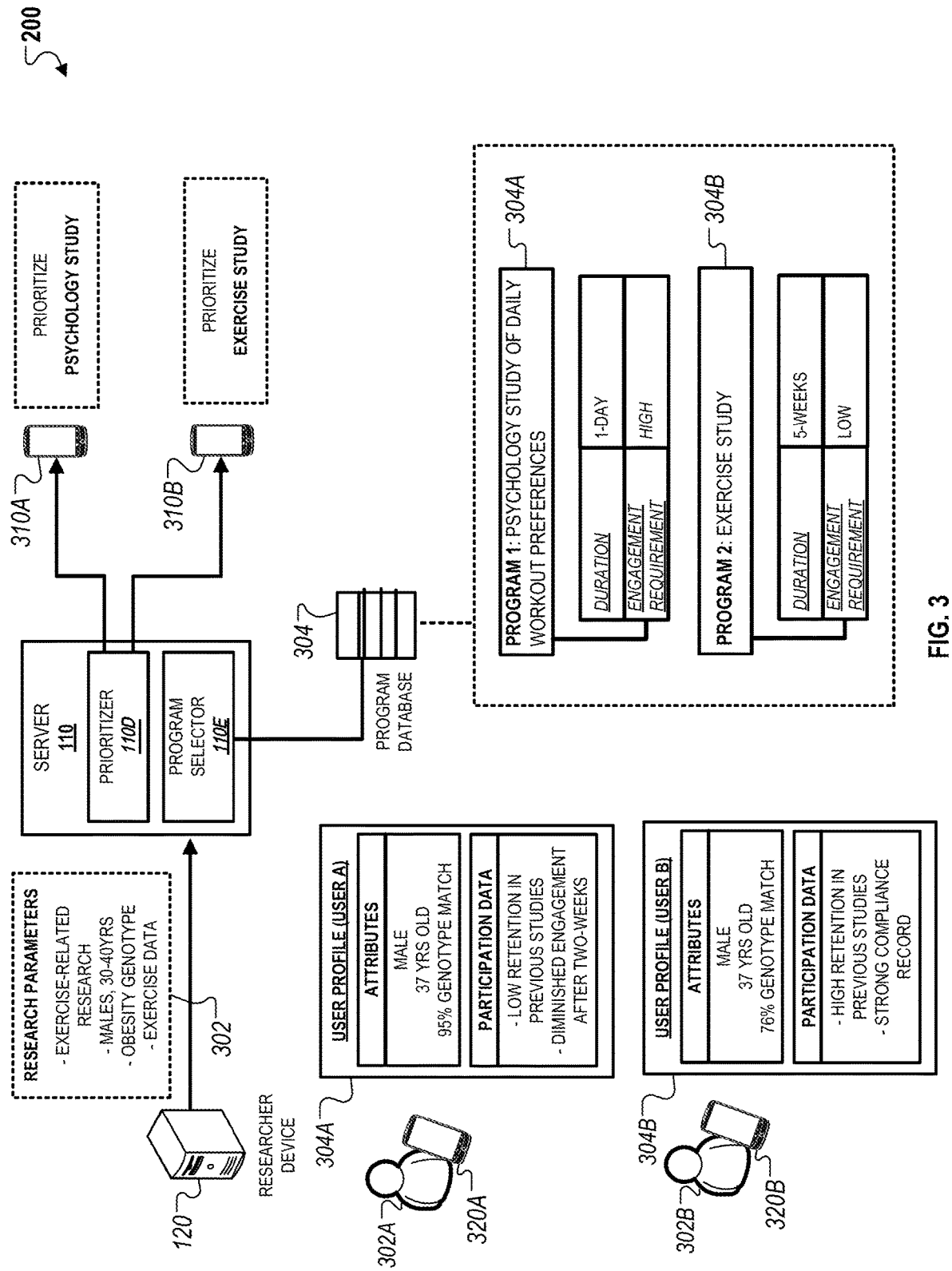
FIG. 3 illustrates an example of a technique for customizing the prioritization of program opportunities for two users.

FIG. 3 illustrates an example of a technique 300 for customizing the prioritization of program opportunities for two users 302A and 302B. In the example, users 302A and 302B are similar in terms of their demographic profiles (both users are 37-year-old males) but have different participation data, as shown in user profiles 304A and 304B, respectively. For example, user profile 304A indicates that user 302A has low retention in previous research studies and diminished engagement in research studies after a two-week time period. In contrast, user profile 304B indicates that user 302B has high retention in previous studies and has strong compliance in the research studies he/she has previously enrolled in.

In the example shown in FIG. 3, server 110 includes a prioritizer 110D and a program selector 110E, which collectively customize a program to prioritize for reach user based on research parameters 302 received from the researcher device 120 and information specified in user profiles 304A and 304B. Research parameters 302 specify a research focus (exercise-related research), target participant attributes (males aged between 30-40 years), a genotype preference (obesity factors) and the type of data to be collected (exercise data).

As described throughout, the server 110 identifies program opportunities for users 302A and 302B by identifying relevant programs within program database 304. In the example shown in FIG. 3, the server 110 identifies two programs 304A and 304B from the program database 304 as being relevant for prioritization for program opportunities for users 302A and 302B. In this example, program 304A is a psychology study of daily workout preferences that requires a one-day commitment for participation and has a high engagement requirement since participation in the study involves completing user surveys detailing a user's past experiences relating to workout preferences. Program 304B is an exercise study that requires a five-week commitment for participation but has a low engagement requirement since a user is required to provide data once a week summarizing their weekly exercise activity.

The server 110 prioritizes programs 304A and 304B using similar techniques discussed in reference to FIGS. 2A and 2B. In this example, the server 110 customizes prioritization for each user and in relation to the research parameters 302. Thus, the server 110 balances the research parameters 302 and the preferences of each user in a different fashion, which results in different prioritizations being provided to each user.

For example, the server 110 prioritizes the psychology study (i.e., program 304A) for user 302A since this user's participation data indicates low retention in previous research studies and diminished engagement in longer-term studies. The server 110 thereby predicts that user 302A is unlikely to successfully complete program 304B (which would then result in a bad outcome for the researcher). The server 110 determines to prioritize program 304A for user 302A even though the user has a 95% genotype match to the obesity genotype specified in the research parameters. In this example, the prioritization is based on a higher emphasis being placed on likelihood of study competition compared to the selection of the most eligible cohort candidates.

In the second example, the server 110 instead prioritizes the exercise study (i.e., program 304B) for user 302B since this user's participation data indicates high retention in previous research studies and a strong compliance record. The server 110 thereby predicts that the user's participation in program 304B would be beneficial to both the user 302B (based on his/her historical activity) and the researcher (by enrolling a participant in a valuable research study with a high likelihood of completion). In this example, the prioritization is based on a higher emphasis being placed on a mutually beneficial outcome rather than a specific focus for the user.

In some implementations, program prioritizations for individual users can be generated based on prioritizations that are generated for other similar users that are also seeking program enrollment. For example, in FIG. 3, the prioritization for user 304A can be generated based on a prioritization that has already been generated for user 304B. In this example, the server 110 may determine to prioritize program 304A over program 304B since it has already prioritized program 304A to user 304B. Thus, while user 302A is a stronger genotype match for program 304B compared to user 302B (95% match compared to 76%), the server 110 nonetheless prioritizes program 304A since there is another user with a reasonably strong genotype match. This technique can be applied to other techniques that allow evaluation of program enrollment of individual users based on potential enrollment of other users.

Figure 4:
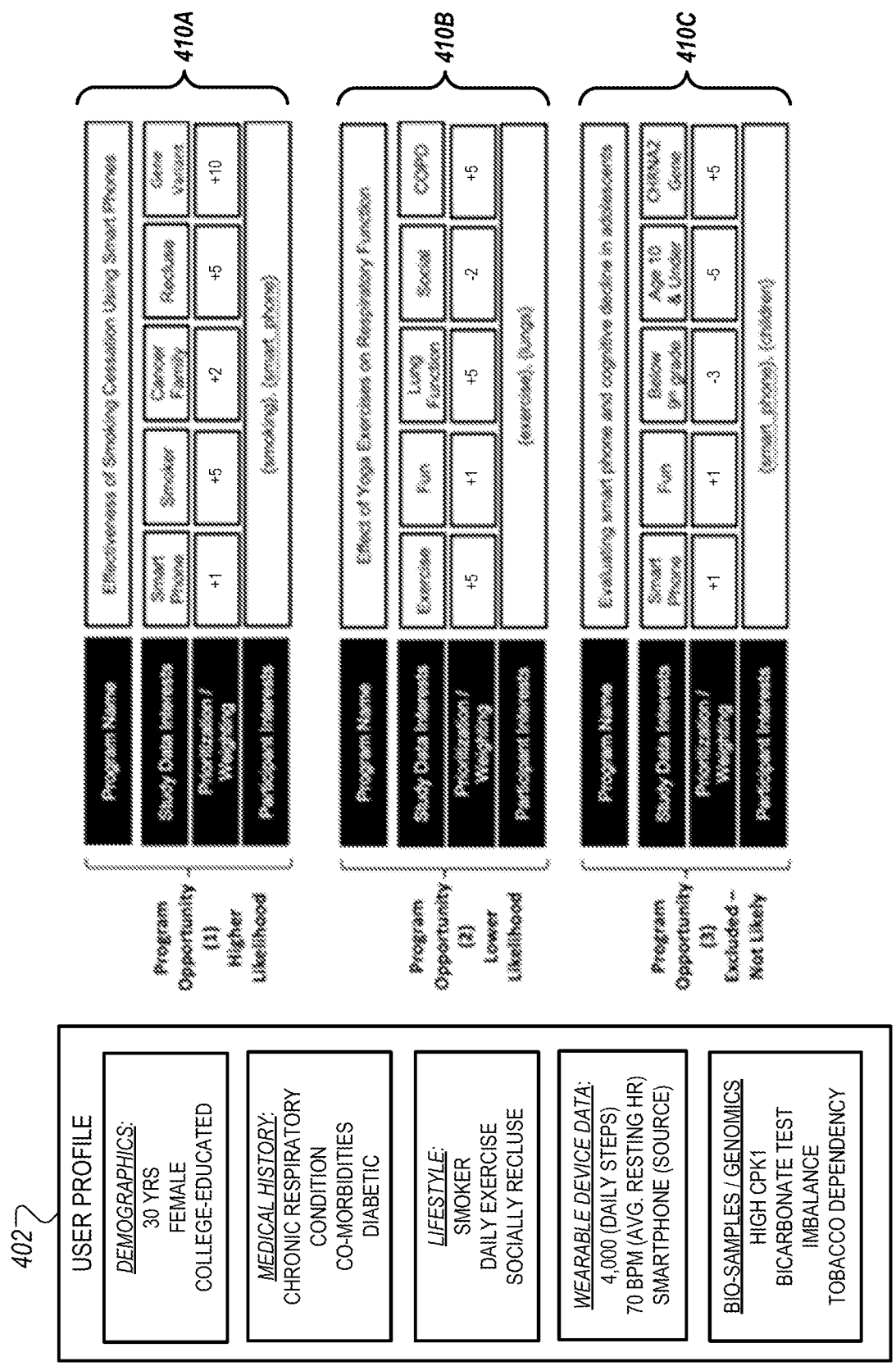
FIG. 4 illustrates examples of program profiles that be used in prioritizing program opportunities.

FIG. 4 illustrates examples of program profiles 410A, 410B, and 410C, which are evaluated in relation to a user profile 402. Program profiles 410A-C are used to prioritize corresponding programs in relation to a program opportunity. As described throughout, programs are prioritized by predicting, based on user data (e.g., data specified in a user profile) and research requirement data, whether user participation in a given program will produce a mutually beneficial outcome for the user and the researcher.

In the example shown in FIG. 4, information specified within each program profile is evaluated relative to information specified in user profile 402 to rank each program. In this example, a program corresponding to program profile 410A has the highest rank (relative to the programs corresponding to program profiles 410B and 410C). This program is ranked the highest since it is related to smoke cessation and the user's participation in this program may benefit the user's overall health and because the study data interests within the program profile 410A includes a strong preference for a specific gene variant specified within the user profile 402. Thus, given the user's attributes, the user's participation in the program is predicted to mutually benefit both the user and the researcher that conducts the research. As shown in FIG. 4, this is reflected in model 410A using weights assigned to attributes associated Program profile 410B is ranked to have the second-highest priority since its corresponding program is focused on evaluating the effect of yoga exercises on respiratory functions. This program is identified as being relevant to information included in the user profile 402 since the user participates in daily exercise and has a chronic respiratory function (which may help the user if he/she participates the program). However, the user profile also indicates that the user is socially recluse yet the study data interests indicate a desire to recruit patients that are social (and therefore likely to continue participating in the exercise program with others). Using weighting techniques discussed above, the system therefore determines that the program is of lower priority compared to the program corresponding to the program profile 410A.

Program profile 410C is ranked to have the lowest priority since its corresponding program is focused on evaluating smart phone and cognitive decline in adolescents. This program is identified as being relevant to the user since it relates to smartphone activity and user profile 402 indicates that the user uses a smartphone. However, the user also does not satisfy participant criteria for education (below 9th grade level education) and age (age 10 and under). Negative weights are therefore assigned to these criteria to reduce the overall prioritization of the program.

Figure 5A:
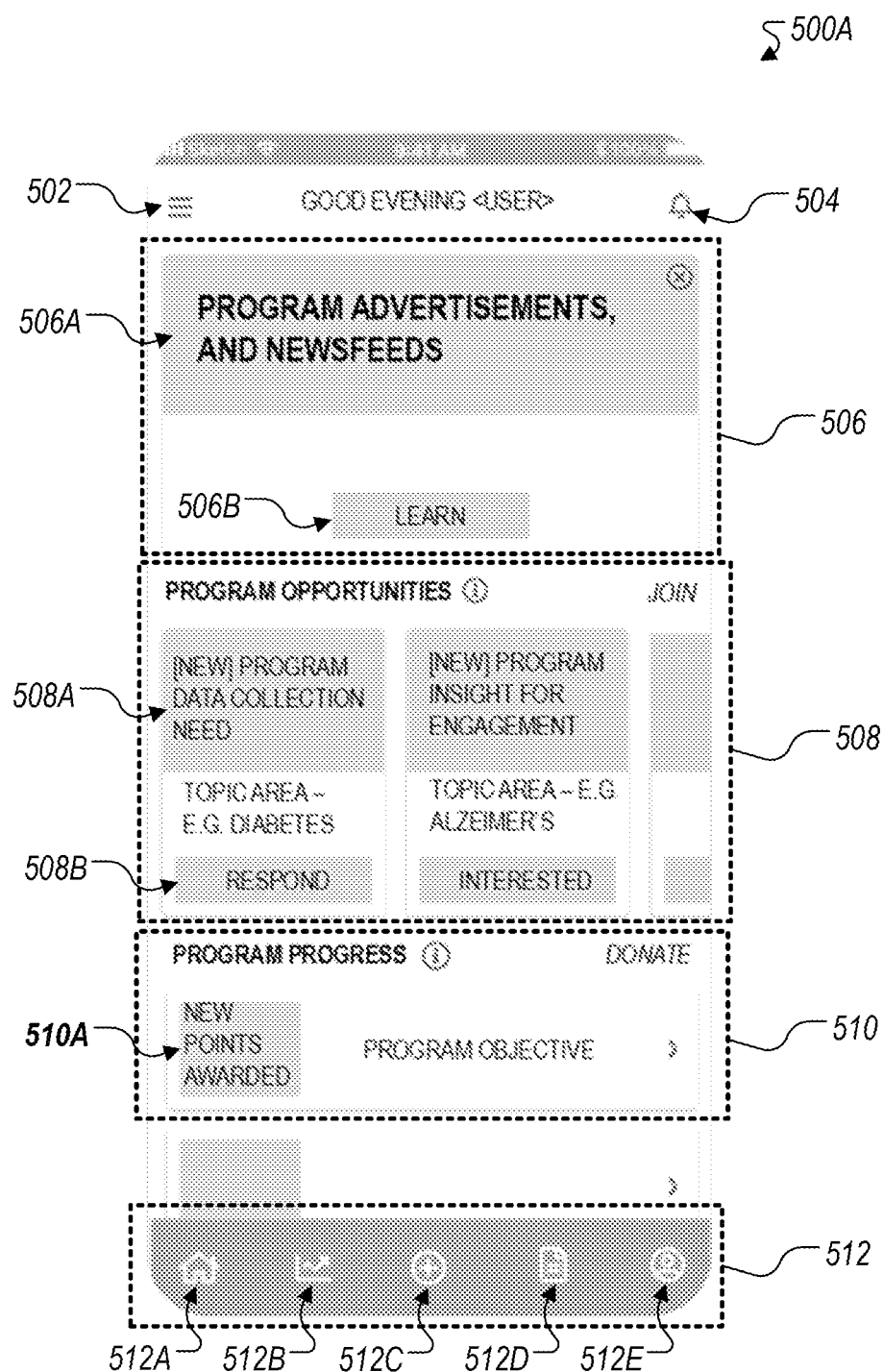
FIGS. 5A-5C illustrate examples of user interfaces that provide information related to program opportunities and selection result data for prioritized programs.
Figure 5B:
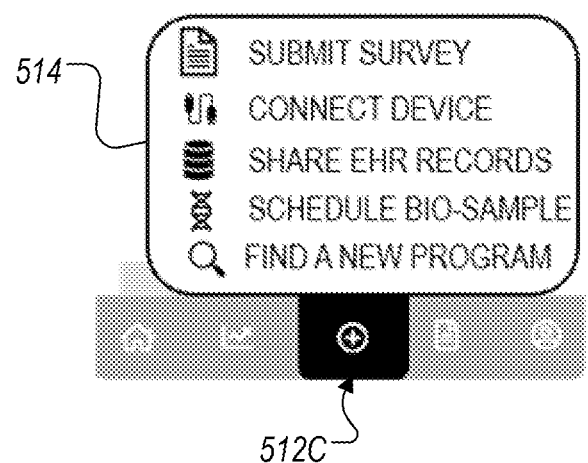
Figure 5C:
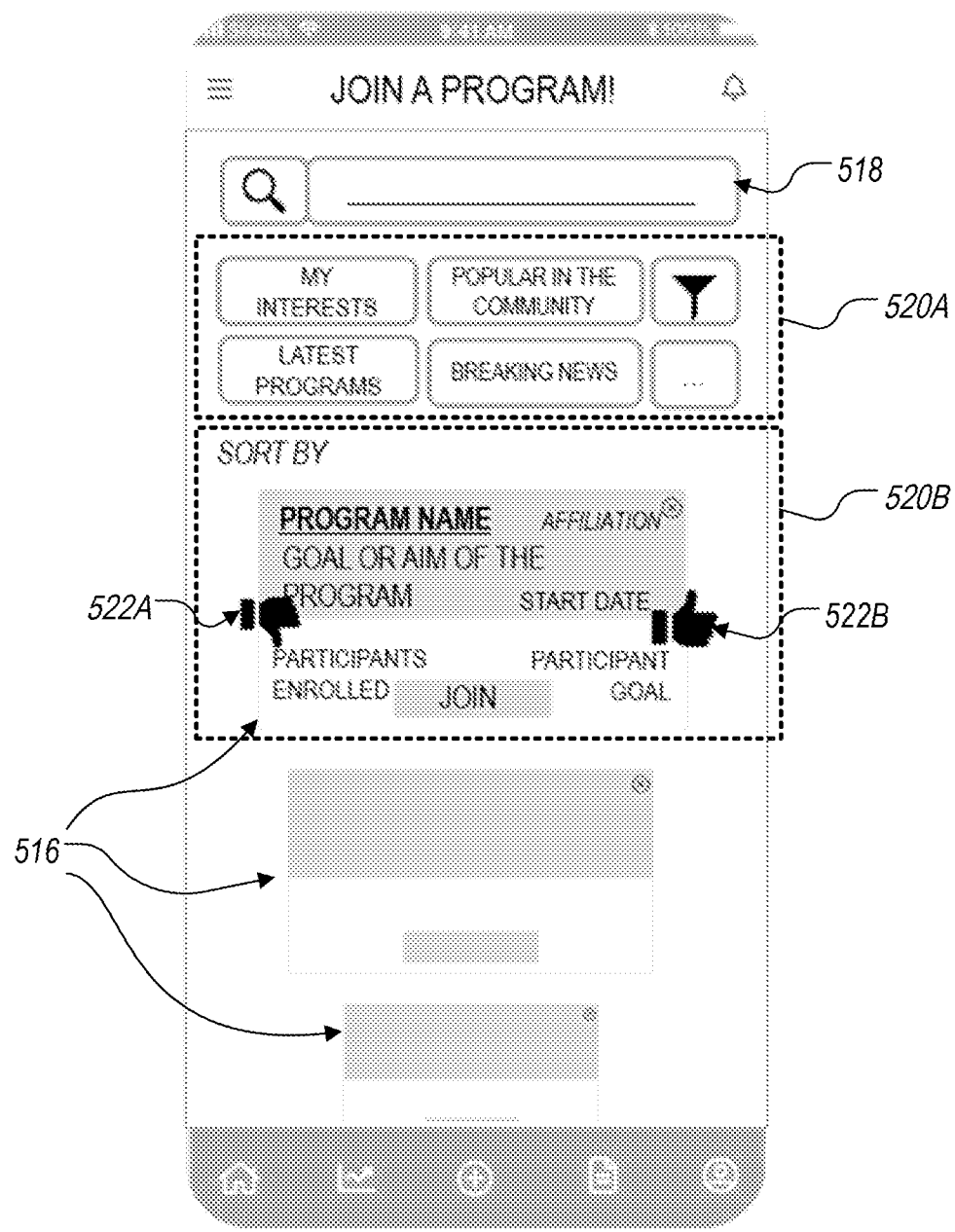

FIGS. 5A-5C illustrate examples of user interfaces 500A-500C that provide information related to program opportunities and selection result data for prioritized programs. Each of interfaces 500A-500C can be provided through a computing device, such as device 130 shown in FIG. 1A. In some implementations, interfaces 500A-500C are accessed through a mobile application running on the device 130, while in others, the interfaces 500A-500C are accessed through a webpage through a web browser application.

In general, interfaces 500A-500C and present information related to programs that in the form of a gallery generated by a server (e.g., server 110) based on processing user data and research requirement data (as depicted in FIG. 1A). The programs selected by the server can be based on user data incorporating different data collection techniques, such as data collected by user interaction with surveys, wearable devices, personal devices, user profiles, EHR software, among others.

Program information can be presented through interfaces 500A-500C at different time points of the program participation process. In some instances, program information is presented before users register to participate in a program. In such instances, program information presented through interfaces 500A-500C can be used to sponsor registration or recruitment of a program by incentivizing the user's participation. In other instances, program information is presented while the user is participating in a program to, for example, maintain user engagement within the program, indicate other program opportunities that have recently become available and may be better aligned with a user's objectives. Program information can also change over time based on various factions, such as new program opportunities become available, user interests changing over time, a user's progress advancing through a program, or changes in research requirements for an ongoing program. In such circumstances, interfaces 500A-500C can provide customized recommendations relating to program opportunities based on such changed program information.

Referring initially to FIG. 5A, an interface 500A for viewing information related to program opportunities is shown. Interface 500A allows a user, e.g., a candidate participant to which program information is provided, to engage with program information through multiple channels, such as recent informational updates, opportunities, and completed engagements.

The interface 500A includes an option 502 that allows a user to access configuration and settings related to receiving program information. Option 504 allows a user to configure notifications related to program opportunities. Interface 500A also includes regions 506, 508, 510, and 512 that enables different types of user interactions with program information.

Interface region 506 includes a newsfeed 506A that provides information related to program news and advertisements. An engagement action 506B allows a user to engage with information presented through the newsfeed 506A, such as learning more about the presented information.

Interface region 508 includes information cards 508A for program opportunities identified by the system. For example, an information card identify a research need for a program, topic areas associated with the program, an option 508B enabling user interaction with the information card. As described throughout, program information included in the information cards 508A can be selectively provided based on identifying programs that are mutually beneficial for the user and/or a researcher associated with a program. For instance, as discussed in reference to FIG. 1A, the system can select a program that is likely to both be relevant to user interests and provide a research benefit based on the user participating in the selected program.

Interface region 510 includes progress information for programs that the user is currently participating in. For example, a user may be shown an option 510A that identifies a program objective (e.g., engagement or participation actions needed to be completed to advance in the program) and incentives or rewards associated with competition or satisfaction of the program objective. Information provided through interface region 510 may be used to incentivize user activity relating to program participation, e.g., by identifying points to be awarded to the user if he/she completes actions associated with the program objective.

Interface region 512 includes icons 512A, 512B, 512C, 512D, and 512E for navigating to interfaces related to program information. For example, icon 512A allows a user to access overview and channels for other programs that are accessible through the software platform. Icon 512B allows a user to access data that has been collected for programs that he/she is currently participating in. Icon 512C allows a user to add a program that is shown in interface 500A to a personal watch list. Icon 512D allow a user to access documents relevant to programs that he/she is participating in (e.g., research participation agreements, data collection reports, diagnostic procedure reports, etc.). Icon 512E allows a user to access his/her user profile, which as described throughout, can include various types of user information.

Referring now to FIG. 5B, an interface 500B for interacting with program information is shown. Interface 500B allows a user to navigate through different program opportunities from a dashboard 514. As shown, the dashboard 514 allows a user to find new programs to enroll in, submit a survey, connect a device, share electronic health (EHR) records, and/or schedule bio-sample collection. In some other implementations, the dashboard 514 can allow users to access notification data related to programs to have, for instance, have awareness of new program opportunities.

Referring now to FIG. 5C, an interface 500C for interacting with program selection result information is shown. Interface 500C provides a user with a personalized selection of programs in a set of program cards 516. Each card includes relevant program information that a user can access to determine whether he/she is interested in participating in the program. As shown, a card includes program name, program aim/goal, start data, participants enrolled, and potential participation goals for the user. As discussed throughout, the programs presented in interface 500C are selected based on a combination of evaluating user interests/ preferences in relation to the research requirements of a particular research that conducts or manages the program.

Users can interact with interface elements in selecting a program to participate. For example, a user can access a search box 516 to manually identify programs that are relevant to a specified search query. As another example, the user can access a filter region 518 to filter amongst a set of programs that have been automatically selected by the system as being relevant. As shown, the user can use the filters to identify programs that match the user's interests, programs that have recently opened up for participation, programs that are popular amongst other users, programs that have been covered by recent news stories, among others.

Users can also access feedback regions 520A, 520B to provide feedback on programs that were selected as being relevant to the user and provided through interface 500C. For example, the user can use a dismiss option 522B to indicate lack of interest in participating in a selected option. Alternatively, the user can use a like option 522B to indicate that the selected program information was helpful or interesting. Input relating to options 522A and 522B can be collected by the user's device and used for subsequent program selection. If a user continues to provide negative feedback (e.g., by selecting option 522A) on certain types of programs, e.g., exercise-related programs, then this feedback may be incorporated into future program selection for the user. For example, the system may include a program selection criterion that is assigned a negative weight based on the user previously providing negative feedback for programs have similar attributes (e.g., programs with similar content or subject matter, programs of similar duration, programs conducted by the same researcher or research institution, programs involving the same level of burden to the user, among others). In this example, the system may assign an assign a positive weight to the program selection criterion based on the user previously providing positive feedback for programs having similar attributes.

A user's interactions with options 522A and 522B can be periodically evaluated to passively determine patterns representing use preferences or patterns representing changes to the user preferences. Recognized patterns can be correlated with other information known about the user to make inferences that may be beneficial to program selection for the user. For example, the system may correlate a detected change in a user's interaction data relating to programs involving preventative health management and data indicating that the user has been diagnosed as being pre-diabetic. Based on this correlation, the system predicts that the user's preferences with respect to preventative health management programs may have changed, and as a result, similar programs may be prioritized over other programs that are similar to other programs that the user may have previously participated in.

In some implementations, programs and associated data (e.g., program information, program research requirements) can be adjusted over time, which can then be used to provide users with updated program selections and/or recommendations relating to program opportunities. For example, the system may provide a recommendation for a new program based on therapeutics, for instance, when data collected through a program that a user is currently participating in indicates that an intervention is not working. The newly recommended program can be based on determining that the user's intervention requires adjusting the user's medication titration or dietary needs.

As another example, the system may provide a recommendation for a new program based on readiness, for instance, when exercise data collected through an exercise program indicates that the user's performance has plateaued. The newly recommended program can be based on identifying areas to break the user's plateau, such as a switch to the degree of cardiovascular or strength training, a new exercise regimen that alternates flexibility and balance training, among other types of adjustments.

In some other examples, the system may provide a recommendation for a new program based on digital health technologies (DHT), for instance, when program data relates to a type of wearable device. The newly recommended program can be based on new type of program being available, such as the user accessing a new wearable device, or a new data assessment technique becoming available for collected data. In other examples, the system may provide a recommendation for a new program based on humans research, for instance, when a user may be interested in sharing his/her data with other studies that he/she is not currently participating in. The newly recommended programs can include studies that may benefit from having the user's data being shared for evaluation.

Figure 6:
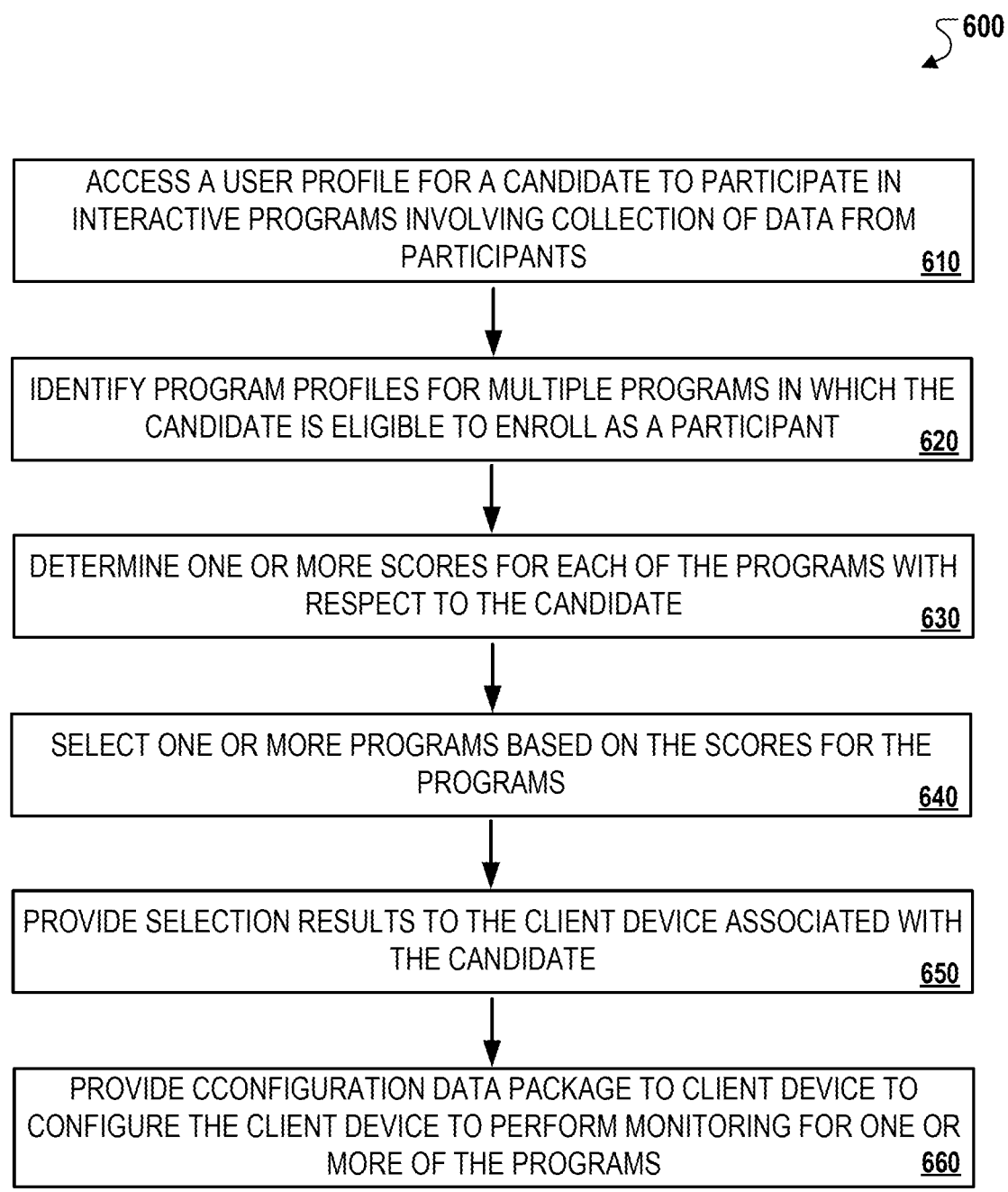
FIG. 6 illustrates an example of a process for identifying and selecting programs for prioritization.

FIG. 6 is an example of a process 600 for identifying and selecting programs for prioritization. The process 600 can be performed by one or more computers, such as a server system such as the server 110. Briefly, the process 600 includes accessing a user profile for a candidate to participate in interactive programs involving collection of data from participants (610), identifying program profiles for multiple programs in which the candidate is eligible to enroll as a participant (620), determining one or more scores for each of the programs with respect to the candidate (630), selecting one or more of the programs based on the scores for the programs (640), and providing selection results to the client device associated with the candidate (650). The process 600 can also include providing a configuration data package to client device to configure the client device to perform monitoring for one or more of the programs (660).

The process 600 can be used by a system, such as the server 110, that is configured to create, recommend, and distribute the software, configuration data, and other content of different programs to remote devices over communication networks, such as the Internet. The programs can be programs that involve repeated, ongoing actions of users and their devices. For example, programs may involve devices taking measurements, monitoring measured values and taking actions in response to detecting certain conditions, reporting collected data to the server 110, providing interactions with users (e.g., prompts, surveys, notifications or alerts, user interfaces, etc.), and so on. Programs may also request or require user actions, including user interaction with their devices (e.g., play a game, complete a survey, and so on).

The program modules that the server 110 provides can cause the devices that receive and install the modules to perform many different types of interactions, for delivery of therapy, for assessment and information gathering, and more. These include interactions that are designed to change the user's behavior, such as to prompt changes to sleep, diet, exercise, medication usage, and other actions that are separate from a user's interaction with devices. The programs can cause targeted interactions that are relevant to the user's current needs or estimated future needs. The interactions can take many forms, and can be based on the content delivered in the original configuration data or program module and/or through later or ongoing communication with the server 110 over a network. A client device used for a program can, either with the module alone or with additional interaction with the server 110, providing media to a user for the user to read or view, generate an interactive form such as a survey, send a notification message or alert, provide a test or assessment of the user, provide recommendations, provide instructional activities or games, provide content from a social media platform, prompt a user to take an action, record a measurement from a device, initiate communication with a health service provider, or communicate with family, friends, or others regarding a user's goals or status. The client device, as directed by the downloaded program module and/or further messages from the server 110, can initiate a challenge to the user, such as challenging, reminding, or informing the user about a goal for the user. The program can involve prompting a user to set, adjust, or view a goal. The interactions of a client device with a user can include interactions involving visual output, audio output, voice input, haptic output, gesture input, and other input/output modalities.

In the healthcare context, a variety of programs can be provided. Examples of health programs include research studies, classes/seminars on health topics (e.g., fitness, nutrition, tobacco cessation, stress management), exercise programs, chronic disease self-management tools, among others. Programs that are predicted to be useful for a user can be prioritized over other programs that are unlikely to be useful so that the user is provided with a customized experience that is tailored to his/her specific needs or interests.

The programs can be designed and implemented to monitor, maintain, and/or improve a user's health and wellness. This includes programs designed to help treat or manage diseases or health conditions, e.g., heart disease, diabetes, cancer, etc. Different programs can be designed and provided for different health conditions and for different types of patients (e.g., different ages, different severities of disease, etc.). The programs may also be used to provide digital therapeutics, including evidence-based therapeutic interventions driven by software programs to prevent, manage, or treat a medical disorder or disease. The programs can be configured to provide contextually relevant interventions to support the health and wellness of a user, can provide adaptive, personalized interventions including content and interactions to improve health of a user.

The server 110 can be used to design and carry out various types of research studies, including observational studies, prospective cohort studies, case-control studies, randomized controlled trials (RCTs), clinical trials, observational trials, longitudinal trials, correlational studies, interventional trials, treatment trials, prevention trials, screening trials, and so on. A program can provide the instructions, software, configuration data, and content to enable a user to enroll in and participate in a corresponding research study. The subject matter of the studies may also vary widely, encompassing studies such as studies of health and disease, pharmaceutical studies, fitness studies, sociological studies, and the like. In some implementations, various different programs offered by the server 110 correspond to different clinical trials. The server 110, in determining how to select and rank opportunities for individuals and devices to participate in the programs representing different studies, can automatically assess satisfying inclusion criteria or exclusion criteria for clinical trials, in real-time and as information available about participants and studies changes.

The programs can represent different research studies with different types of objectives, including different types of trials for drug development. For example, different types or phases of clinical trials can have different objectives, which can affect the types of data to be collected and conditions to be monitored and thus affect the technology options that are selected by the server 110. One program can be for a phase 0 trial, which may be experimental, with the aim to determine how a drug is processed by the body. Another program can be for a phase I trial used to evaluate drug safety and dosage, for example, to find the best dose of a drug that has limited side effects, by gradually increasing dosage until side effects become too severe or positive effects are observed. Another program may be for a phase II trial can be used to assess safety as well as effectiveness of a drug, potentially evaluating effects of a drug in combination with other drugs or other factors. Another program may be for a phase III trial to further assess safety and effectiveness of a drug, for example, to compare effectiveness of a drug with a reference, such as a current standard-of-care drug. As different types of trials have different monitoring and reporting needs, the server 110 can use these parameters to determine the profiles for the corresponding programs and to tailor the recommendation and distribution of programs accordingly.

The techniques in the present document can be used to define study parameters and select cohorts for studies that involve further data collection, in which cohort members provide data for a period of time after the study begins, e.g., often a defined period time such as several weeks, months, or even years. The techniques can also be used to define study parameters and select cohorts for studies that are based on previously collected or generated data.

Today, only 5% of the US population participates in clinical research. With the rise of new software tools that make research faster, cheaper, and more accessible and with a forward-looking FDA digital health team, the time is ripe for a clinical trial paradigm shift. One of the advantages of the systems described herein is the ability to assist in software-enabled clinical trials, e.g., clinical trials that involve mobile applications, web interactions, and other software. The systems described herein can be used for remote clinical research, such as when participants in a study are located remotely from the researchers and may be dispersed throughout a country or even across the world. The system provides the scale and precision for clinical grade applications, including use in clinical trials.

The platform and services discussed herein are designed to make clinical trials and registries more accessible and less costly. This can be done by replacing patient visits at investigator sites with technology-enabled interactions at more convenient locations, including patients' homes. Growing numbers of biopharma, life science companies, contract research organizations (CROs), and non-profit researchers need a virtual research platform to capture clinical study data in between clinic visits, as well as during or instead of clinic visits. The platform supports an integrated suite of user-friendly, highly configurable applications that provide interfaces to obtain electronic consent (e.g., "eConsent") from individuals, collect electronic patient-reported outcomes (ePRO) or provide electronic clinical outcome assessment (eCOA), patient engagement, telehealth virtual visits, site data capture, and medical device and consumer sensor connection. The platform enables researchers to modernize clinical research for customers, participants, and sites, and makes virtual research approaches the standard in studies and registries.

In more detail, the process 600 includes accessing a candidate profile (e.g., user profile) for a candidate to participate in interactive programs involving collection of data from participants (610). The server 110 can generate, store, and update user profiles for many different individuals, including former, current, and prospective participants in monitoring programs. The user profile for a user can include various attributes about a user, including demographic attributes, physiological attributes, behavioral attributes, contextual attributes (e.g., location, residence, etc.). In further detail, the profiles may include information such as: (1) demographics (e.g., age, ethnicity, race, gender, etc.); (2) health and medical history (e.g., pre-existing conditions, intake encounter information from electronic medical records (EMR)/electronic health records (EHR)); (3) family history (e.g., conditions, death-related risks, family origins); (4) data describing a user's lifestyle (e.g., exercise levels, smoking status, alcohol use, drug use, extravert, introvert, social network characteristics); (5) environmental data (e.g., air quality, mineral deposit, lead in the water, etc.); (6) wearables and devices of a user (e.g., watch, trackers, monitors, assessment tool reports, etc.); (7) insurance claim data (e.g., encounters, frequency, medications); (8) clinical data—(e.g., bio-sample data, test results); (9) genetic analysis (e.g., gene variants), and (10) microbiome data.

The user profile can also indicate records of activities of the user, including behavior patterns and whether actions of the user during participation in prior monitoring programs complied with the requirements of those monitoring programs. For example, if the user was enrolled in a prior study that involved collection of three different types of data, the user profile can include records indicating the accuracy, reliability, consistency, and other characteristics of data collection for each of the three data types. The user profile can include information indicating how closely the data collection met the level requested by the monitoring program, such as a proportion or rate of collection that was performed effectively.

The user profile can also include user interests, such as topics, keywords, search terms, and other indicators of subjects that the user is interested in. The user profile can also include preferences of the user, whether expressly indicated by the user or not. For example, in some implementations, the server 110 can update a profile based on actions of user to dismiss a recommendation of a program, to view details of a program then decline to participate, actions to agree to participate in past programs, and so on. The history of which program descriptions a user has viewed or selected in the past can provide the server 110 information about what the user would be interested in or would be willing to participate in in the future.

The user profile can also include information about the types of devices that the user has or has experience using. In general, this information about the user's devices, as well as the capabilities of those devices and the user's usage history of them, can be a significant indicator of the ability of the user to comply with monitoring program requirements that involve user of those technologies.

The user profile for a user can also include information specifying the amount or types of activities that a user would be willing participate in a single program or for all programs combined. One of the aspects of the selection and ranking of programs by the server 110 is to account for the burden that each candidate program would cause if the user enrolled in the program. For each user, the server 110 determines the capacity or availability of the user to participate in programs, for example, measures of the extent that a user is willing to participate in programs, such as the amount of time, types of interactions, frequency of interactions, and other parameters the user is expected to actually spend. As an example, the server 110 may determine that a particular user is willing to spend a total of 3 hours a week, including two interactions (e.g., surveys) through a device each day. This information can be stored in the profile for the user, and then the server 110 can later compare the requirements of individual candidate programs and groups of candidate programs to the estimated capacity or availability of the user.

The server 110 can estimate the amount of capacity or availability of a user based on the historical data indicating the extent that other users have successfully participated in other programs. For example, the server 110 can identify profiles of a group of other users that have similar attributes to a user and determine the amounts of time, types of interactions, types of data collection that have been successful or unsuccessful, frequency of interactions, and so on for users in the group. The aggregate information for the group, e.g., the average, maximum, minimum, distribution, etc. for different measures of participation in programs (e.g., amount of time, types of data collected, types of activities performed, types of devices used, etc.) can be used to set limits or ranges on the burden that the user is likely to accept. This allows, for example, the system to infer the level of involvement that a user will be capable of and likely provide, based on other users that have similar attributes (e.g., demographic attributes, physiological attributes, behavioral attributes, location, interests, etc.) and history (e.g., involvement in past programs, etc.).

In some implementations, the server 110 can generate models of different clusters of users to indicate the capacity or availability generally for users of those types, and the models can be updated and refined as additional data is received. In some implementations, the server 110 can generate and user machine learning models to predict the capacity or availability of a user, trained based on examples of how various users have behaved. The input can include attributes and history of a user and the output can be scores, classifications, or other indicators of the level of capacity for dimensions of participation (e.g., amount of time, frequency of interaction, types of interaction, types of data collected, etc.). Each training example can include an input data set (e.g., a vector of input feature values) describing attributes and/or activities of a user and a target label representing the actual participation that resulted from the user (e.g., amount of time, types of data, and interactions successfully and consistently achieved). The machine learning models can then be used to predict the capacity and availability for users either to set values in the user profiles or in addition to the information in the user profiles.

The server 110 can also update the information about a user's capacity or availability with information specifically about the user. If a user has signed up for a program that involves 2 hours per week of commitment but only participates for 1 hour a week, the server 110 can update the profile to specify that the user is only available for 1 hour a week. If a user has signed up for a program that involves 2 hours a week of activity and the user spends this time consistently, the server 110 may infer that the user has availability for this much commitment or more, and indicate in the profile that the user has 2.5 or 3 hours of availability each week. Similarly, the server 110 can adjust which activities (e.g., games, types of surveys, media viewing, etc.) or types of data (e.g., blood pressure collection, blood glucose data, heart rate, etc.) the user is likely to collect with accuracy and consistency. The information in the profile can go beyond what the user has the technical capability to collect with a device, and instead indicate the type and level of user action that is likely to be performed with accuracy, consistency, and reliability needed for monitoring programs. Even if a user is known to have a watch that can measure exercise (e.g., step count) and heart rate, if the user's device usage data shows that the user does not regularly wear the watch or that the user failed to consistently provide this data in a prior program, the profile for the user can indicate that these types of data are not available or can penalize the ranking of programs that require this data collection. Thus, the capacity or availability can include measures of expected or predicted user actions that the user would perform in a consistent, repeated basis if needed for a program.

The server 110 has other techniques for estimating availability, such as asking the user directly with a survey or providing a user interface with settings the user can change or preferences the user can specify. For example, a user may be presented a list of data types and the user can check or uncheck items to specify if the user is willing to provide data of those types. Similarly, the user may enter an amount of time the user is willing to spend, a number of interactions preferred per day, and so on.

As the user enrolls in studies, the server 110 tracks how much of the capacity and availability of user is committed to programs, and how much is remaining. For example, if the user has 3 hours of availability per week, and signs up for a program that involves 1 hour a week of activity, the server 110 can update the profile to indicate that only 2 hours a week of availability is remaining. When the server 110 considers the applicability of additional programs to recommend or distribute to the user, the server 110 considers the amount remaining based on the current requirements of programs in which the user is already enrolled. That way, the server 110 can demote or reduce the ranking of programs, or filter out programs, that have requirements that exceed the amount of capacity or available that the user has. This, among other techniques, improves efficiency for both the server 110 and the client device by avoiding the recommendation and distribution of programs to client devices when the device or user is unlikely or unable to comply with the required activities, monitoring, communication, or other elements of the programs.

In many other systems, users frequently download and begin monitoring programs that include elements that they cannot complete, whether for requiring higher levels of time commitment than users can spend, requiring longer duration of ongoing participation (e.g., weeks or months), requiring actions or measurements that are not supported by a user's device, and so on. This leads to significant wasted use of computing resources, such as power, network bandwidth, storage space, and processing time, as client devices perform ineffective partial monitoring and servers perform interactions that are unlikely to yield the long-term monitoring record needed. It can also jeopardize the effectiveness of distributed monitoring schemes, where program administrators may believe that a sufficient number of devices are engaged in monitoring yet a significant portion fail to carry out the needed monitoring, resulting incomplete or unusable data sets. Nevertheless, the present system, by filtering, selecting, and/or ranking programs based on the likely actions of users and their availability and capacity to meet the requirements of different programs, much of the wasteful installations and ineffective partial monitoring can be avoided. The system also improves the user experience by lowering the barrier to entry for user to find and begin new programs. The system can effectively match programs to the interests and capacity of individuals and their devices, avoiding the frustrations and ineffectiveness that result from programs that are overly burdensome for users or devices.

Process 600 includes identifying program profiles for multiple programs in which the candidate is eligible to enroll as a participant (620). The program profiles describe the respective programs and indicate types of data to be collected in the respective programs. More generally, the program profiles can indicate a wide variety of characteristics and parameters of programs, including types of data to be gathered, techniques for gathering the data (e.g., sensors needed, accuracy levels needed, etc.), data collection activities, frequency of data capture needed, level of data quality needed, types of interactions with devices and users, device technical requirements to participate (e.g., hardware and software requirements to carry out monitoring), and so on. Other program parameters include the size of a cohort needed (e.g., minimum and/or maximum numbers of individuals or devices that can participate), duration that the program will be carried out (e.g., 1 month, 3 months, 1 year), scope (e.g., variety or diversity in participant characteristics, contexts, etc.). The program profiles can describe the actions or activities that users or devices are requested to perform or are required to perform as part of participation in a program. This can include actions done through interaction with a device (e.g., complete a daily survey, obtain a measurement with a glucometer, or play a video game) or separately from device interaction (e.g., taking a medication, sleeping for at least 7 hours a night, obtain a current blood test, etc.).

Program profiles can also describe the subject matter of the program. This can include whether a program is for monitoring, treatment, research, or has another purpose. The program profiles can indicate objectives of the programs, including different types of outcomes that are tracked or tested for. This can include different events, conditions, and characteristics that the program is designed to detect, as well as target outcomes that the program intends to achieve for individual participants or for the group of enrolled participants as a whole. For programs representing research studies, the objectives can include a research question or other statement of a relationship to be tested or explored. The study protocol, or information derived from the study protocol, can be included in the program profile, to indicate the requirements for data collection, actions by participants, timing, and other parameters. This information about the nature of programs and the objectives of programs enables the server 110 to determine whether users are likely to contribute to achieving the objective of a program (e.g., if user's data would assist in answering the research question) and if the requirements of a program are a good fit (e.g., sufficiently likely to lead to retention and compliance) if a user or device is enrolled in the program.

As an example, a profile for a program for a clinical trial may have an objective to evaluate the safety of Drug A when administered to healthy adults at 25 mg daily. The profile can include additional information to define the characteristics that qualifies individuals healthy adults (e.g., age at least 18 years old, excluding a list of medical disorders, physiological parameters in certain ranges) as well as the monitoring needed to judge safety (e.g., blood pressure testing twice a day, heart rate monitoring each minute, symptom surveys three times a day). The profile can indicate other actions the user may be required to complete to participate, in addition to taking the medication daily, such as obtaining blood tests, having an in-person visit, and so on. This information and other information about the program enable the server 110 to compare the program information with information about potential participants as indicated the user profiles (e.g., information about interests, attributes, history, preferences, capacity and availability, and so on). It also specifies the elements of the program, both involving interaction with devices and actions and conditions separate from device interaction, so that the server 110 can generate predictions of the likely level of compliance for different individuals with individual elements of the program and for the program as a whole.

The profiles for programs can specify topics, keywords, and other indications of subject matter for a program, including medical conditions or behavior to be studied. The profiles can indicate a needed level of compliance (e.g., 80% of measurements need to be supplied for the data set of a user to be valid) and a minimum likelihood of compliance needed (e.g., a minimum threshold of 75% so that the server 110 does not recommend or enroll participants having a predicted compliance with study requirements, including potentially retention to the end of the duration of the study). The importance of each user completing a program varies for different programs. For some programs, the commitment of computing resources is minimal (or many participants are available or useful data is still obtained through only partial compliance), so recommending and distributing the programs to users is appropriate even if there is low likelihood of compliance with the elements of the program. The program profiles can indicate this with a low weight given to compliance metrics or low minimum thresholds. For other programs, however, the costs of a user enrolling and failing to complete the program are high, such as due to high computing resource consumption, limited specialized devices being needed or limited licenses available for use, or for other reasons. In these cases, the program profiles can weight compliance and retention factors highly and include high minimum thresholds to apply to the predictions for different users when assessing suitability.

The program profiles also describe the types of user and devices that are needed for a program, including selection criteria such as inclusion criteria for including individuals in a cohort for a research study or exclusion criteria for excluding individuals in a cohort for a research study. For clinical treatment programs and digital therapeutics programs, the program profiles can indicate the patient characteristics, medical conditions, diagnoses, indications and contra-indications, etc. that qualify or disqualify a person for the program. In general, the program profiles can set thresholds, ranges, classifications, or other criteria with respect to any of the types of data included in participant profiles (e.g., demographic attributes, physiological attributes, behavioral attributes, history, medical history, family medical history, genetics, etc.).

Another portion of the program profiles can indicate weightings of different requirements or elements of the program and for different candidate participant attributes. For example, a program may have certain strict selection criteria (e.g., user must have an age 18 or older, must have a smartphone, etc.). In addition, the program may have other elements that are preferred to different degrees but are not strictly required. For example, a program for a research study may prefer candidates in Alabama, candidates with a family medical history of heart disease, and candidates with a certain rare gene variant. These different attributes may have different weightings or levels of preference, however, such as +1.5, +5, and +10 respectively. The weightings in the profiles can be used to score the different candidate profiles and boost (or penalize) the relevance of the program to a candidate profile by the amounts indicated by the weightings. The presence of multiple of these factors can be combined. For example, a user that is in Alabama can have a boost of +1.5, a candidate in Alabama with the rare gene variant can have a boost of +11.5, and so on. For efficient processing, the system can store a vector of weighting values (e.g., relevance adjustment factors) for each profile, where values in the vector specify the different amounts of relevance boost or penalty for different possible candidate attributes, and during scoring the weight vector can be multiplied with a one-hot vector indicating which of the relevant candidate attributes are present.

In addition to weighting participant attributes, the profiles can include weight values or boost/penalty adjustment factors to indicate the relative importance of different data to be collected, for different device capabilities (e.g., different importance of different sensor types), and generally for any other elements. Similarly, weight values for study elements or study parameters can indicate the importance of compliance with different program requirements. For example, compliance with a heart rate monitoring requirement may be very important (e.g., weight of 10) while blood pressure monitoring compliance may be low or optional (e.g., score of 1). The profile may also specify more complex relationships among participant attributes, compliance predictions, and study elements, including context dependence. For example, the importance of location in selection may have weight value of 1 when in one age range and have a weight value of 2 for a different age range. As another example, blood pressure monitoring may not be required (or may be weighted as low importance) for candidates unless the candidate has diabetes or certain other medical conditions, in which blood pressure capability may be required and compliance likelihood or predicted compliance rate may be required to be at least 70%.

Weight values may be determined in various different ways. For example, an administrator or research may initially set preferences and specify the relative importance of different factors (e.g., of the study and of potential candidate devices and users). The server 110 can then normalize the factors across the different programs to provide for more comparable scoring. Through use over time or through simulations the server 110 can incrementally adjust the weights in the profiles of different programs, so that the server reaches an equilibrium or balance in which most or all of the programs have at least a minimum level priority or relevance among a minimum number of candidates. For example, if in the analysis the server 110 determines that a program is not in the top 10 most relevant programs for a sufficient number of users, the server 110 can incrementally boost the weight values (or incrementally broaden the selection criteria if the program creator permits) to be able to reach an appropriate candidate pool. Similarly, if users are not enrolling in a program (e.g., a research study) at the needed rates (e.g., in the needed amounts or timing to fill a cohort), the server 110 can similarly gradually boost the weight values to increase relevance for the program and cause it to be shown more often and more prominently, in order to assist in filing the monitoring group (e.g., cohort) needed to meet the monitoring objective of the program.

Process 600 includes determining one or more scores for each of the programs with respect to the candidate (630). The scores for each program can be based on various different factors, such as (i) relevance or value of the program to the user, (ii) relevance or value of the user to the program, (iii) prediction of compliance with requirements, (iv) predicted data quality from the user enrolling in the program, (v) burden resulting from a program and a user's capacity or availability, (vi) costs or limitations of enrollment, (vii) a current status of the candidate, program, or enrolled group from the program. In some implementations, the server generates a different score (e.g., a component score or factor score) for each of the different factors for each of the programs. For each program the server 110 combines the component scores into an overall score that indicates the suitability or appropriateness of the program and candidate for each other (e.g., taking into account compatibility, relevance, likelihood of successful completion, degree or likelihood of compliance with program elements, etc.). For example, the overall score can indicate how well the two profiles match, e.g., the degree that the program meets the needs of the candidate and how well the candidate meets the needs of the program. In some implementations, rather than determine separate scores for the different factors, the server 110 uses a scoring function or scoring module that directly calculates the score for a program with respect to a candidate. As discussed further below, the scoring can also be done using machine learning techniques, using models that the server 110 trains based on the observed data collection, program compliance, and selection of programs by users.

In further detail, the server 110 can assess relevance or value of a program to the user. This includes determining the presence of matches between topics, keywords, and other data from the user profile with data describing the program in the program profile. It also includes assessing the health status of a user (e.g., physiological attributes, diabetes, overweight, health goals the user set, etc.) and determining how well the program fits the user's health needs. For example, the server 110 can determine that a user has diabetes and determine whether and to what extent the program profile indicates that it treats or helps manage diabetes (e.g., for a clinical treatment program, care plan, or digital therapeutic). Similarly, the server 110 can determine the value that a program can provide to a user given the user's health, history, and other data. For example, if a user has diabetes and a research study program provides educational materials and repeated updates about diabetes status, this can be a significant benefit for the user. The potential benefits to the user can be in terms of information provided, physical health improvement, mental health improvement, and more.

The server 110 can also assess the relevance or value of the user to the program. For many programs, such as research studies, data collected from individuals with different backgrounds has different levels of value to the study. Some individuals are excluded from participation and would provide no benefit by being in a cohort. Others are eligible for a cohort but have characteristics that are average or perhaps only qualify as a control for comparison with users having another more specific set background. And in some cases there are specific combinations of attributes that make the data from a user particularly important for a study. For example, a study to test the effectiveness of a medication on heart disease would need individuals with heart disease with which to test the effectiveness. In other cases, specific personal medical history, family medical history, genomics characteristics, proteomics characteristics, lifestyle or behaviors, or other factors may make a user particular suitable for one study or another. Even for therapeutic programs, the provider may be interested in having patients with certain profiles, to test effectiveness of the program for those profiles or because the program provides the greatest effectiveness for individuals with those profiles. Using the weight values in the program profile, the server 110 can assess the level of fit between the various attributes in a user profile and the set of attributes that make a candidate's data set more or less valuable to a program. The weight values for the factors that are present in a candidate's profile can be combined, e.g., summed, averaged, or otherwise aggregated. Program profiles may also include selection criteria, contraindications, or other factors that may exclude a program from being relevant for a user. Beyond a simple adjustment to a score, a user failing to satisfy the selection criteria or a user having an attribute that disqualifies the user can cause the program to be removed from consideration for the user.

The server 110 can generate predictions regarding the likelihood and extent of compliance by a candidate with a program. This can include predictions for specific elements (e.g., activities, types of data to collect, etc.) or for retention of the candidate to completion of the study. This can be based on the combination of attributes that a user has, and the compliance observed for individuals with similar combinations of values for the attributes. For example, the compliance results for a subset of individuals having attributes determined to be similar to those of the candidate can be used to determine the likely level of compliance. For example, the average among the group of similar individuals can be used as the estimate. As another example, a machine learning model can be trained and used by the server 110, based on examples of different individuals and their actions over time.

As discussed above, the server 110 has information about user compliance and data quality from data collected in programs that are ongoing or which have completed, and from research literature. Based on the historical device usage or compliance information, and information about the individuals enrolled in programs earlier, the server 110 can determine which attributes are predictive of different levels of compliance with different program elements (e.g., different types of sensor data collection, different types of interactions, taking medication, etc.) rates of different technologies. For example, the usage of a particular model of smart watch may vary according to user age, while the completion of a survey may vary according to education level or location. The server 110 can perform statistical analysis to determine the correlations between different attributes and combinations of attributes with the resulting compliance of individuals with different elements of different programs.

In some implementations, the server 110 can generate rules or scoring functions based on the relationships determined through analysis of study cohort characteristics (e.g., attributes of individuals or groups), the elements of programs, and the outcomes (e.g., usage measures, data quality, compliance with study protocols, etc.). The server 110 can then use the rules or scoring functions to generate or adjust suitability scores for the programs based on the attributes that are determined to affect the results for compliance with program elements. For example, the server 110 may determine that the rate of successful use of one device is affected by age of participants, while the rate of successful use of another device is affected by the location of participants. From these relationships, the server 110 can set rules or scoring functions that reward or penalize the suitability of different technologies when considered for use with individuals of certain attributes or combinations of attributes. For example, the server 110 can set scoring factors, offsets, weightings, or other values that will adjust the suitability score of a program for an individual when the individual has certain attributes.

In addition to statistical or rule-based analysis, or as an alternative, the server 110 may also learn relationships between individuals' attributes and technology items using machine learning. For example, the server 110 can train one or more machine learning models to predict the likelihood of compliance with one or more elements of a program (e.g., achieving a result such as collecting and reporting a desired type of data with appropriate data quality) based on subject attributes. One or more machine learning models can be used to generate the suitability scores, as discussed further below. As with all other machine learning models discussed herein, the one or more machine learning models may include at least one of a neural network, a support vector machine, a classifier, a regression model, a reinforcement learning model, a clustering model, a decision tree, a random forest model, a genetic algorithm, a Bayesian model, or a Gaussian mixture model. Each of the models discussed below may be trained using examples from research literature, programs designed or carried out using features of the server 110, or other examples.

As one example, the server 110 can train a machine learning model to predict a score or likelihood of successful compliance with a program element by one or more individuals, based on input feature values indicating attributes of the one or more individuals. For example, a neural network can have an output layer that provides values that respectively correspond to various different technology items. Given input of feature values indicating a set of attributes, the neural network can produce a score (e.g., a likelihood of compliance by an individual, a compliance or usage rate for a group, etc.) for each of the different elements of a program that is based on the attributes indicated by the input. As another example, a model may be structured to receive input indicating attributes of one or more individuals and data that describes and/or identifies a specific element of a program. In response, the neural network can process the data to determine a score (e.g., usage likelihood, compliance or usage rate, etc.) for the specific element of the program indicated at the input. As another example, different models can be generated for different program elements, each model being trained to receive input indicating attributes of one or more individuals and provide an output score for the predicted compliance for the program element that the model corresponds to. The score for predicted compliance can be combined with, e.g., weighted with or used to adjust, a score for a program element or for the program as a whole.

In some implementations, a machine learning model uses attribute information to generate a suitability score for a program. For example, a model can combine the evaluation of how well a program meets a user's needs with the evaluation of how likely the program is to be used effectively by an individual.

Along with prediction of user compliance with actions that are part of a program, such as taking medication, performing behaviors needed (e.g., sleeping, exercising, etc. in a manner specified by the program, completing surveys, using a wearable device, etc.), the server 110 can also predict data quality from the user enrolling in the program in the same manner. For example, through analysis or machine learning the server 110 can assess the accuracy, precision, reliability, completeness, and other aspects of collected data of individuals, to estimate the level of quality of data that a user's participation in a program will provide. If the quality level is less than a desired level for the program, the program can be removed from consideration for the candidate (e.g., filtered out of the set) or can be penalized in ranking among other programs.

The server 110 can assess the potential burden resulting from the candidate enrolling in a program. As discussed above, the server 110 can track user's capacity or availability, both in the aggregate for all programs and for an amount remaining that may be allocated for a new program. The server 110 can compare burden factors such as the total amount of time a program requires over a time period (e.g., each day, each week, etc.), the number of interactions, the types of interactions, and so on in the program profile with the remaining capacity or availability of the user. If the requirements of the program exceed the capacity and availability of the user, then the program's score is penalized. The greater the program exceeds the user's capacity and availability, the greater the penalty. As a result, a program that requires 2 hours a week when the user only has 1 hour a week to spend may not be filtered out completely, but there would need to be significant other factors to balance it out for it to be recommended to the user (e.g., very high value or relevance to the user, the user having background or set of attributes that is in high demand for the program, etc.).

The server 110 can assess costs or limitations of enrollment by the user in the program. For example, some programs may require sending the user an expensive device, or may involve limited computing resources. Given these costs, some programs may be more strict in the thresholds that are required for compliance predictions or other factors.

The server 110 can assess a current status of the candidate, program, or enrolled group from the program. The scoring of programs can take into account the most recent data about the program and the candidate being considered. The state of a program can affect how it is recommended. For example, if 500 people are needed for a cohort, and none have been selected, the scoring can indicate a higher value for the program to recruit a particular user than if the same user had been considered after 450 people had already enrolled.

The server 110 can also consider the relative value that a user provides to different programs. For example, a user may be equally interested in and qualified for two different programs, with similar overall (e.g., combined) scores. Nevertheless, to meet its monitoring objective, a first program may require many more participants than a second program, or may have selection criteria that limit the candidate pool more drastically than the second program. As a result, the server 110 may favor the selection and ranking of the first program, since the candidate may be more important to the more restrictive first program, because there are other candidates that can easily fill the monitoring group of the second program but the program profiles may indicate that the user's specific background is more rare and more valuable to the first program. This type of analysis can allow the server 110 to make tradeoffs among programs on a candidate by candidate basis, allowing the server 110 to more intelligently assist each of the programs to fill their needed minimum levels of participation among a limited number of candidates, where the candidates each have limited capacity or availability to participate in programs.

Process 600 includes selecting one or more of the programs based on the scores for the programs (640). Using the scores and analysis discussed in step 630, the server 110 can filter out programs that are incompatible for a candidate, which would not meet the objectives of the program (e.g., would not help treat the candidate or the candidate would not be eligible for the research study cohort), or which would provide a likelihood or extent of compliance or data quality below a minimum threshold. The server 110 can select a subset of the programs considered based on the scores, such as by ranking the programs based on the overall suitability scores of the programs for the user. In some cases, the highest ranking subset (e.g., the top 5 or top 10) are selected and provided.

In many cases, the interface of remote devices that communicate with the server 110 is of a very limited size, admitting only a limited information about a program that is described or recommended. Especially when provided in a gallery or list, the small screen size of mobile devices such as smartphones precludes displaying much of the information that a user would need to determine if a program is a good fit (e.g., required activities, health indications and contraindications, duration of participation needed, data types, etc.). As a result, the server's ability to analyze these factors is an important advantage, since the server 110 can take these factors into account to provide the most applicable programs. As noted above, this generally includes ranking or filtering the program selections to a set of programs that impose a burden on the user that is less than or equal to the remaining availability of the user, which helps avoid users signing up for programs that they cannot continue and imposing inefficiency on their devices and on the server 110. Similarly, the use of compliance predictions for the programs also limits the set of programs selected for recommendation or distribution to programs that the viewing user will have a high likelihood of completion.

In some cases, the server 110 can adjust the weighting of different component scores or analyzed factors in determining the selection and ranking of programs. For example, for some programs or some users, different weighting values may be used to adjust the level of influence that different factors have on the overall score for the programs for ranking. One program may use a high weight to show that the compliance factor is most important, while another program may have a low weight for compliance but a high weight for the data quality prediction.

Process 600 includes providing selection results to the client device associated with the candidate (650). The server 110 can send data indicating the selected programs and their rankings to the client device associated with a user over a communication network, such as the Internet. The selection results can be provided as a customized list of programs that are displayable at the client device. The list can be ranked according to the scores, to indicate the best overall fit for the user at the top, or otherwise indicate it more prominently. Along with the indication of the program (e.g., a name, logo, or other identifier), the data for display can include an indication of a provider (e.g., hospital, doctor, research institution, university, etc.), a brief description of the program, or other information. In some implementations, data is displayable so that selection result for a program includes user interface controls for a user to approve or select the item, to see a larger information panel or UI describing the program and/or to initiate enrollment of the candidate and to obtain the needed software or configuration data to initiate the program.

The selection results can be provided through different interfaces and communication modalities. For example, the selection results can be generated and provided in response to a user of a client device navigating to a user interface for a gallery of programs, with the selection results populating the gallery. As another example, the programs can be evaluated independent of user action with a device, and one or more programs (such as the highest-ranked program) can be indicated to the user at any time, potentially in a message through email, text message, chat functionality, and so on.

Process 600 includes providing a configuration data package to client device to configure the client device to perform monitoring for one or more of the programs (660). Ultimately, a primary objective of the server 110 is to distribute to remote devices the software and configuration data needed to enable the devices to begin the monitoring and interactions needed to meet the objectives of the respective programs provided and managed by the server 110. After the server 110 recommends a set of programs for a user, the user may select one or more of the recommended programs and the server 110 receives this input. In response, the server 110 can retrieve and send the configuration data for the selected program to the client device, causing the client device to install or otherwise make the program active. In some implementations, client devices first install a base application that is configurable to perform any of the various programs offered by the server 110, and then once a program is selected, the configuration data package includes the instructions, settings, procedures, and content that enable the application to carry out the monitoring and interactions of that program.

For example, a configuration data package can specify which sensors to activate, and under which conditions and which schedule. The configuration data package can also specify which measurement data to save, the format of the data, the precision needed, etc. The configuration data package can also specify surveys and other user interactions to provide, as well as the timing for providing these. The configuration data package can indicate types of connected devices to connect with, and the types of data to obtain from them (e.g., weight from a weight scale, blood glucose data from a glucometer, etc.). In general, the configuration data package can include software modules, device settings, device drivers, communication settings (e.g., specifying network protocols, timing and content of messages reporting collected data to the server, network addresses and ports for providing data over the network, etc.), parameters for data collection, and more. The configuration data package can be configured so that, when a device having the base application installed receives the configuration data package, the application automatically applies the appropriate configurations from the package to initiate monitoring and interactions of the program.

While various actions are described herein as being performed by the server 110, the actions may be distributed among other devices. In many cases, the actions may be performed by the client devices of different users. For example, program profiles can be send to remote devices, and the remote devices can perform the scoring of programs, ranking of programs, recommendation of programs, and display of programs. Client devices can request and receive configuration data from one or more servers to obtain the configuration data needed to begin the monitoring, treatment, user interactions, or other actions needed to participate in a program.

Figure 7:
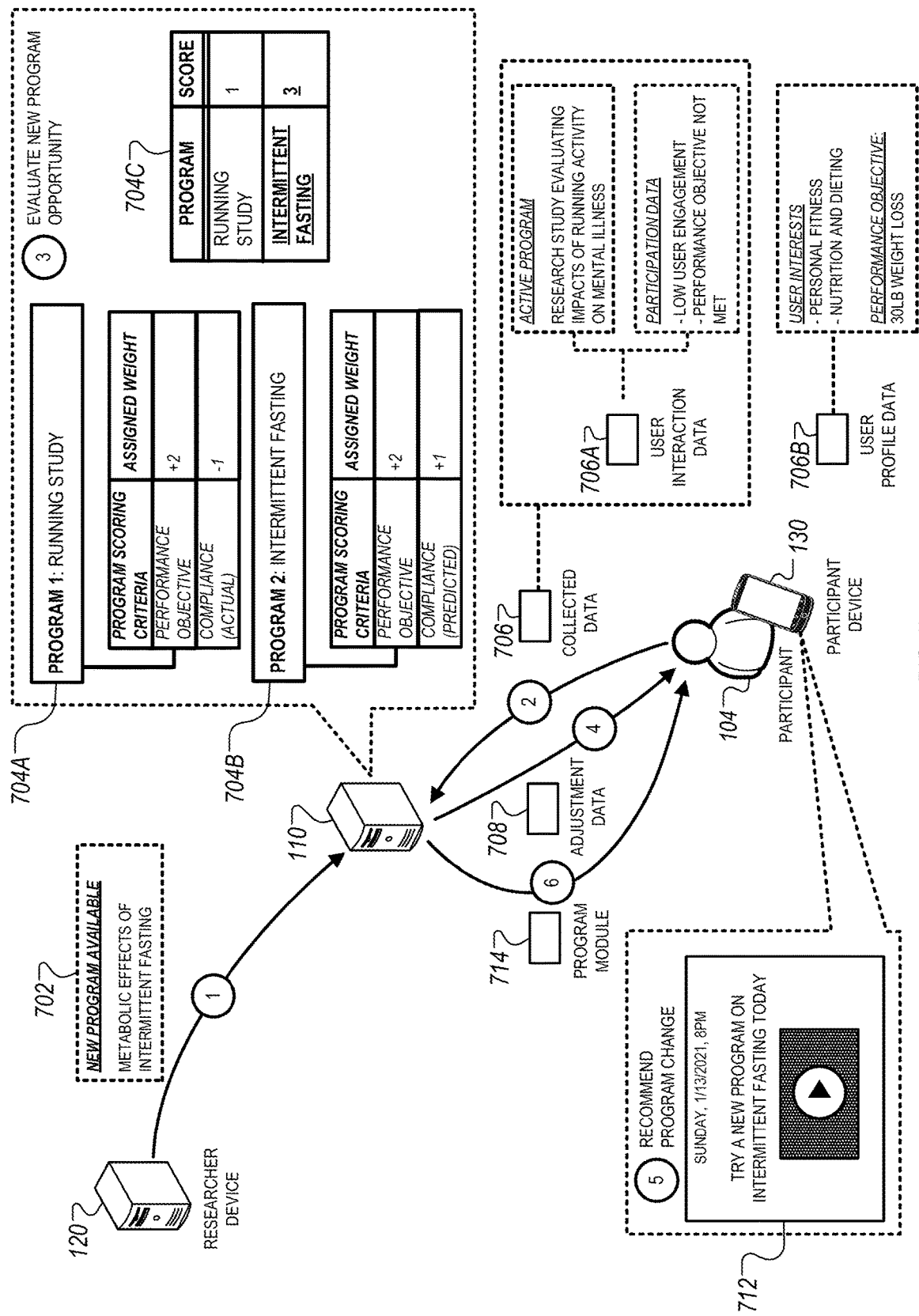
FIG. 7 illustrates an example of a technique for recommending an adjustment to user participation in an active program based on evaluating a new program opportunity.

FIG. 7 illustrates an example of a technique for recommending an adjustment to user participation in an active program based on evaluating a new program opportunity. As described throughout, an "active" program refers to a program that a user has currently enrolled in, a program that a user is participating in, or a program that a user has agreed to enroll in but has not yet began participation. The system can designate a program as being active once a user provides input to confirm participation in the program. For example, if a user is currently participating in a program for an ongoing research study, then the program is designated as active given the user's participation in the ongoing research study.

The technique shown in FIG. 7 proceeds in a set of steps. At step 1, the server 110 receives an indication 702 of a new program opportunity from the researcher device 120. The new program opportunity relates to program 704B for a prospective research study relating to the metabolic effects of intermittent fasting. In this example, program 704B is developed on researcher device 120 while user 104 is already enrolled and participating in program 704A for a research study evaluating impacts of running activity on mental illness. The server 110 thereby receives the indication 702 at while the user continues to participate in program 704A. In this example, program 704A is designated by the server 110 as an active program.

At step 2, the server 110 obtains collected data 706 associated with an active program. The collected data 706 includes monitoring data collected during user participation in program 704A, such as user interaction data 706A. The user interaction data 706A identifies program 702A as an active program (i.e., a program for which user 104 is currently enrolled). The user interaction data 706A also includes participation data that was collected by the device 130.

In the example shown in FIG. 7, the collected participation data indicates that the user had low user engagement represented by, for example, a reduced number of detected user interactions with the device 130 while participating in program 704A compared to the user's interactions with the device 130 while participating in other studies. The collected participation data also indicates that a performance objective for the program 704A was also not met. The performance objective can represent a user goal for participating in program 704A, such as weight loss goal as a result of participating in program 704A. Other examples of performance objectives include completing a number of interaction modules available through a program, providing a certain amount of monitoring data to be used for a research study, among others.

The collected data 706 also includes user profile data 706B. The user profile data 706B may be stored at the server 110 and used to indicate information associated with user 104, such as user interests and performance objectives associated with user participation in program 704A. In the example shown in FIG. 7, the user profile data 706B identifies the user's interests in personal fitness and exercise and the user's performance objective of losing thirty pounds while participating in program 706B.

At step 3, the server 110 evaluates a new program opportunity based on assessing the collected data 706. In the example shown in FIG. 7, the server 110 evaluates the program opportunity by using a set of program scoring criteria to compare a user's ongoing participation in program 704A with possible user participation in program 704B. In this example, the server 110 evaluates the new program opportunity by assessing the collected data 706 and determining that the collected data 706 satisfies a condition for adjusting program participation. For example, given that program 704A relates to fitness, the condition may be that the user's measured performance (weight loss by user 104) not meeting a target performance objective (thirty pound weight loss). In this example, the server 110 determines that continued user participation in program 704A may not be beneficial to user 104 since his/her participation has not produced performance that satisfies the user's performance objective (thirty pound weight loss).

As shown in FIG. 7, the system uses program scoring criteria to adjust user participation by prioritizing participation in program 704B over continued participation in program 704A. This prioritization is based on the user's participation in program 704B producing a beneficial user outcome, such as meeting the user's performance objective of losing thirty pounds. To accomplish this, the server, computes weights for two criteria relating to user outcome. The performance objective criteria refers to a likelihood that a user's participation in a corresponding program will result in the user meeting a performance objective specified in the user profile data 706A. The compliance criteria represents a likelihood of user complying with the requirements specified by a program. The weights computed for each program based on the criteria are then combined in table 704C and used to identify a recommendation regarding the new program opportunity.

In the example depicted in FIG. 7, the server 110 generates weights for program 704A based on information specified by the user interaction data 706A. For instance, given low user engagement in the participation data, the server 110 assigns a negative weight (−1) to the compliance criteria for program 704A since there is a low likelihood that the user will continue to engage and/or be compliant with the remainder of program 704A. In contrast, the server 110 assigns a positive weight for the compliance criteria for program 704B since, for instance, user information within either the user interaction data 706A or the user profile data 706AB may suggest that user 104 is likely to comply with requirements of program 704B. For example, the user profile data 706B may identify other programs related to program 704B (e.g., programs relating to intermittent fasting) that the user 104 successfully completed, which suggests that he/she may comply with the requirements for program 704B. As another example, user interaction data 706A may include survey data indicating that the user 104 has a stronger preference for adjusting his/her diet as a way to lose weight compared increasing his/her exercise regimen to lose weight. The server 110 may use this and other types of indicators to assign a positive weight to the compliance factor for program 704B. The server 110 combines the assigned weights to compute a score for each program in table 704C.

The server 110 uses scores computed for each program in table 704C in recommending a program change for the user. In the example shown in FIG. 7, the server 110 determines a score value of 3 for program 704B and a score value of 1 for program 704A. In this example, the score value represents the outcome of an assessment by the server 110 of the likelihood of user participation in a program as producing a beneficial outcome for the user, and specifically, the likelihood of meeting the user's performance objective of losing thirty pounds. The server 110 uses the score values to determine that user participation in program 704B provides a better opportunity to meet the user's performance objective compared to continued participation in program 704A. The server 110 uses this assessment to generate a program change specifying a recommendation to adjust user participation from program 704A to program 704B.

At step 4, the server 110 generates adjustment data 708 and provides the adjustment data 708 to device 130. The adjustment data 708 includes a recommendation to adjust user participation in program 704A based on the scores identified in table 704C. The adjustment data 708 may include instructions that cause an application on the device 130 to provide an interface (e.g., interface 712) relating to the program change.

At step 5, the device 130 provides an interface 812 with a program change selected by the server 110. As shown, the interface 812 includes a notification informing user 104 of the new program opportunity relating to program 804B. The interface 812 also includes an option 812A that allows the user to enroll in program 804B based on providing a user input.

In this way, the user 104 can be notified of programs that may be a better use of his/her time in participating in programs. For example, as discussed above, by enrolling in program 704A, the user 104 may have a better chance of meeting his/her performance objective of losing thirty pounds given that program 704B relates to intermittent fasting (which more closely aligns with his/her interests in nutrition and dieting).

In some instances, the server 110 may determine that user participation in program 704B is a better use of the user's time compared to continuing participation in program 704A since the user is more likely to be engaged when participating in program 704B. In such instances, the interface 712 includes, for example, a recommendation to adjust program participation such that the user 104 exclusively dedicates his/her time in participating in program 704B. In other instances, for example, where the user's time is not a limiting factor, the interface 712 includes a recommendation to supplement participation in program 704A with program 704B (so that the user participates in both programs in parallel).

At step 6, the server 110 provides a program module 714 for program 704B to the device 130. The program module 714 is customized for the user 104 and/or the device 130 and configured to allow the user 104 to participate in program 704B. In the example shown in FIG. 7, the server 110 can use settings to customize the manner by which the user interacts with the program to improve, for example, user engagement, user retention, or the likelihood of obtaining a successful outcome (e.g., meeting the user's performance objective of losing thirty pounds).

Figure 8:
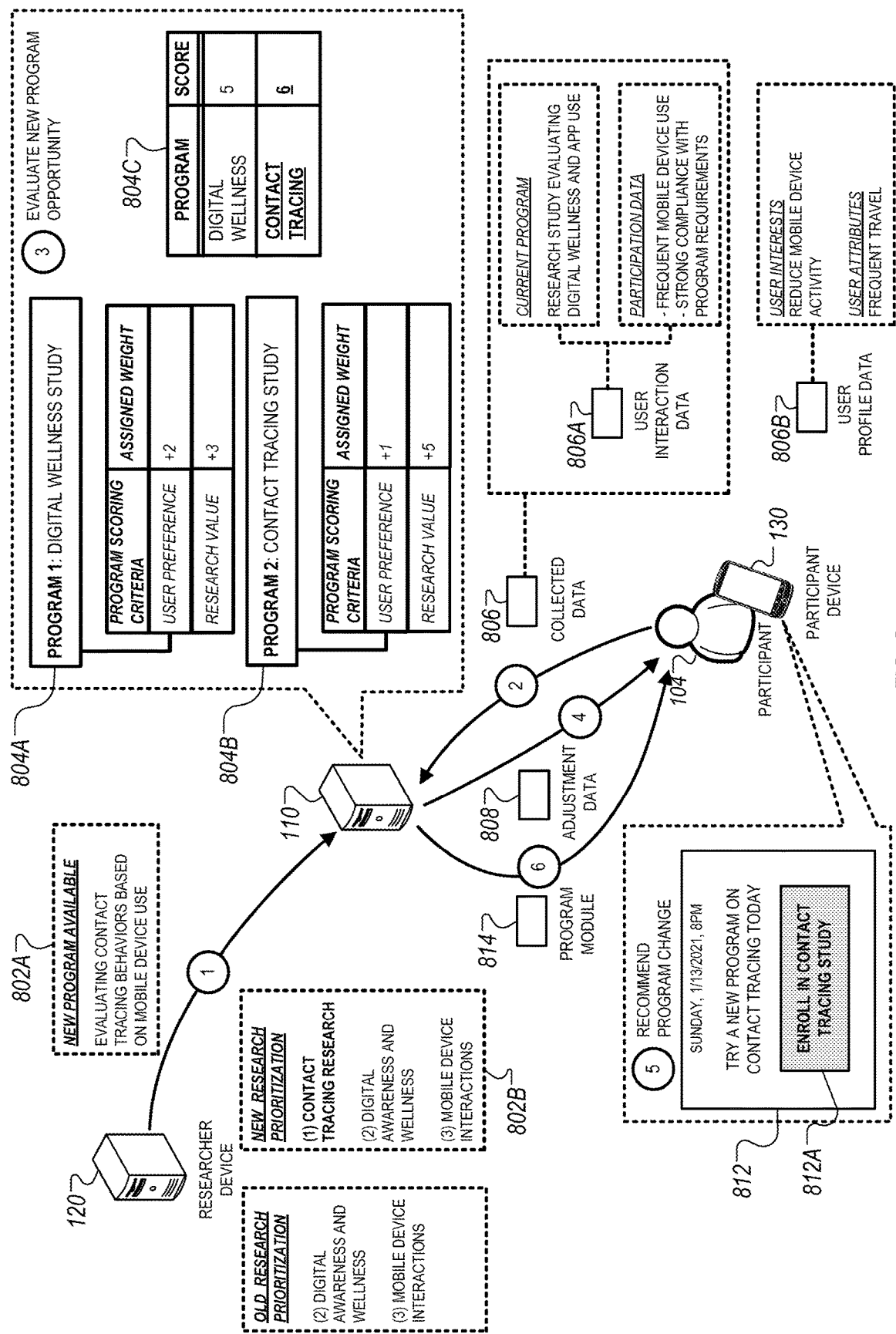
FIG. 8 illustrates an example of a technique for recommending an adjustment to user participation in an active program based on a change to research prioritization.

FIG. 8 illustrates an example of a technique for recommending an adjustment to user participation in an active program based on a change to research prioritization. In this example, the server 110 determines that the adjustment may be beneficial to a researcher based on a recent change to research prioritization. While a user's participation in the active program may support a research objective of the researcher, the adjustment may further improve the impact of user participation given the change in research prioritization while also benefiting the user.

The technique shown in FIG. 8 proceeds in a set of steps. At step 1, the server 110 receives an indication 802A of a new program opportunity from the researcher device 120. The new program opportunity relates to program 804B for a prospective research study relating to evaluating contact tracing behaviors based on mobile device use. In this example, program 804 is a developed by a researcher that also manages program 804A relating to a research study evaluating digital wellness and application use. The server 110 receives indication 802A while the user continues to participate in program 804A. In this example, program 804A is designated by server 110 as an active program.

The server 110 also receives an indication 802B of a new research prioritization. The indication 802B specifies a new research priority for contact tracing research, which has now become more important that prior research priorities relating to studying digital awareness and wellness or mobile device interactions. In some instances, the researcher device 120 identifies the new research prioritization specified in the indication 802A based on manual input provided by the researcher. In other instances, the researcher device 120 may passively identify the new research prioritization based on new research studies becoming available and being focused on a certain research topic.

At step 2, the server 110 collects user data 806 associated with the active program 804A. The collected data 806 includes monitoring data collected during user participation in program 804A, such as user interaction data 806A. The user interaction data 806A identifies program 802A as an active program (i.e., a program for which user 104 is currently enrolled). The user interaction data 806A also includes participation data that was collected by the device 130.

In the example shown in FIG. 8, the collected participation data indicates that the user has had frequent mobile device use while participating in program 704A and a strong compliance with requirements of program 704A. The server 110 determines from this information that user participation in the program 704A is beneficial to the user since the participation data indicates that the user 104 is engaged in the program. However, given the new research prioritization specified in the indication 802B, the user's participation may be helpful in other programs that are more aligned with the new research prioritization.

The collected data 806 also includes user profile data 806B. The user profile data 806B may be stored at the server 110 and used to indicate information associated with user 104, such as user interests and performance objectives associated with user participation in program 804A. In the example shown in FIG. 8, the user profile data 806B identifies the user's interests reducing mobile device activity and a user attribute of frequent travel.

At step 3, the server 110 evaluates the new program opportunity based on assessing the collected data 806. In the example shown in FIG. 8, the server 110 evaluates the program opportunity by using a set of program scoring criteria to compare a user's ongoing participation in program 804A with possible user participation in program 804B. In this example, the server 110 evaluates the new program opportunity by assessing the collected data 806 and determining that the collected data 806 satisfies a condition for adjusting program participation. For example, even though the participation data indicates that the user is sufficiently engaged in program 804A, this program is a research study relating to digital wellness, which is now a secondary research priority for the researcher (as specified by indication 802B). In this example, the condition may be tied to the new research prioritization specified by indication 802B, which results in the server 110 evaluating whether user participation in other programs, such as program 804B, may provide stronger research alignment with the new research prioritization.

As shown in FIG. 8, the system uses program scoring criteria to adjust user participation by prioritizing participation in program 804B over continued participation in program 804A. This prioritization is based on the user's participation in program 804B having stronger alignment with the researcher's new research prioritization. To accomplish this, the server 110 computes weights for two criteria relating to research prioritization. The user preference criteria refers to a likelihood that user participation in a corresponding program supports user interests specified in the user profile data 706A. The research value criteria represents a benefit of participation data to a user's research prioritization. The weights computed for each program based on the criteria are combined in table 804C and used to recommend a program change.

In the example depicted in FIG. 8, the server 110 generates weights for program 804A based on information specified by the user interaction data 806A. For instance, given the user's engagement while participating in program 804A, the server 110 assigns a positive weight (+2) to the user preference criteria for program 804A. The server 110 assigns a lower positive weight (+1) for the user preference criteria for program 804B since the research subject for this program (e.g., contact tracing) is less relevant to the user interest in reducing mobile device activity compared to the research subject for program 804A. Additionally, since research subjects of programs 804A and 804B are both related to research prioritizations, the server 110 assigns positive weights for the research value criteria for both programs. However, the server 110 assigns a higher weight (+5) for this criteria for program 804B since this program relates to the highest priority research topic (contact tracing research). The server 110 combines the assigned weights to compute a score for each program in table 804C.

The server 110 uses scores computed for each program in table 804C in recommending a program change to the user. In the example shown in FIG. 8, the server 110 determines a score value of 6 for program 704B and a score value of 3 for program 704A. In this example, the score value represents the outcome of an assessment by the server 110 of the likelihood of user participation in a program as producing research value. The server 110 uses the score values to determine that user participation in program 804B creates a stronger research value given the new research prioritization that is focused on contact tracing research. The server 110 uses this assessment to generate data indicating a recommendation to adjust user participation from program 804A to program 804B.

At step 4, the server 110 generates adjustment data 808 and provides the adjustment data 808 to device 130. The adjustment data 808 includes a recommendation to adjust user participation in program 804A based on the scores identified in table 804C. The adjustment data 808 may include instructions that cause an application on the device 130 to provide an interface (e.g., interface 812) relating to program adjustment.

At step 5, the device 130 provides an interface 812 with a program change selected or recommended by the server 110. As shown, the interface 812 includes a notification informing user 104 of the new program opportunity relating to program 804B. In this way, the user 104 can be notified of programs that may be a better use of his/her time in participating in programs. For example, as discussed above, by enrolling in program 804B, data generated by the user device 130 can produce a stronger value to the researcher compared to data generated from the user's participation in program 804A.

At step 6, the server 110 provides a program module 814 for program 804B to the device 130. The program module 814 is customized for the user 104 and/or the device 130 and configured to allow the user 104 to participate in program 804B. In the example shown in FIG. 8, the server 110 can use settings to customize the manner by which the user interacts with the program to improve, for example, collection of data relating to contact tracing research.

Figure 9:
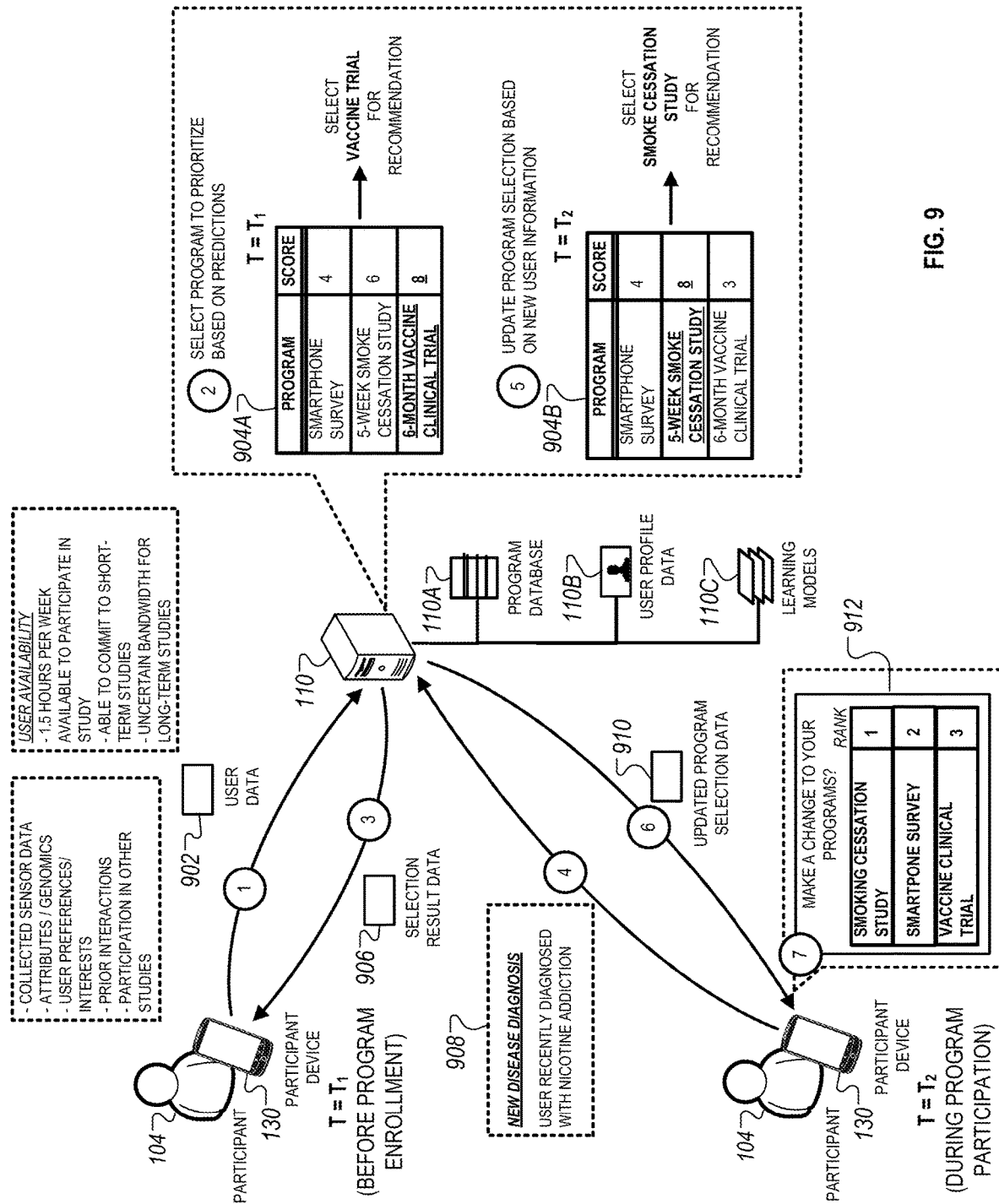
FIG. 9 illustrates an example of a technique for predicting and distributing program changes within a software platform.

FIG. 9 illustrates an example of a technique for predicting and distributing program changes within a software platform. The server 110 prioritizes program opportunities for programs available for participation by a user. Once a user enrolls in a program, the server 110 continues to collect data (e.g., user data, participation data, program data) that is then used to update the prioritization of program opportunities on an ongoing basis. In the example shown in FIG. 9, the server 110 generates two different program recommendations at two time points—a first time point ($T_1$) before program enrollment, and a second time point ($T_2$) once a user has enrolled in a program and is continuing to participate in the enrolled program. As shown, the server 110 generates different recommendations at each time point based on changes to a user's needs and data collected based on user participation in the enrolled program. Using these techniques, the server 110 can dynamically prioritize program opportunities at any point in the enrollment process (e.g., before enrollment of a program, during program participation, after a user has recently completed a program).

The technique shown in FIG. 9 proceeds in a set of steps. At step 1, the server 110 receives user data 902 from device 130. The user data 902 includes various types of information associated with the user 104. For example, the user data 902 can include sensor data collected by the device 103 and/or a companion wearable device that may be used by the user 104 (e.g., heart rate data, pedometer data, accelerometer data, global positioning sensor (GPS) data, etc.). The user data 902 can also include passively sensed data that detected or identified, such as context data, interaction data, cursor movement data, among others. The user data 902 can further specify user attributes or genomics data, such as demographic information, previously diagnosed conditions, physiological attributes, phenotypical information, or medications currently being taken by the user. Additionally, the user data 902 can include interaction data (e.g., data indicating how and when the user 104 interacts with graphical user interfaces provided on the device 130), and study participation data (e.g., research studies that the user 104 previously participated in or compliance or retention information associated with the research studies).

At step 2, prior to program enrollment, the server 110 selects a set of programs 904A from the program database 110A for prioritization based on the program opportunities predicted by the learning models 110C. In the example shown in FIG. 9, the learning models 110C predict that programs 904A may be beneficial to user 104 based on the information specified by the user data 902. As described throughout, the programs 904A are identified not only because their subject matter aligns with interests of the user 104, but also because user participation may also be beneficial to a researcher (e.g., a researcher associated with device 120, as shown in FIGS. 1A and 1B). In this sense, the server 110 selects programs 904A based on user participation in them mutually benefitting both the user 104 and a researcher to a larger extent than other programs available for enrollment within the program database 110A.

In the example shown in FIG. 9, the server 110 selects to prioritize a program for a vaccine clinical trial research study from among other programs included in the programs 904A based on, for example, a research prioritization of a researcher (not shown). The server 110 makes this selection based on scores computed for each of the programs 904A. As discussed throughout, the server 110 computes the scores by assigning weights to program scoring criteria (e.g., user burden, predicted user compliance, research value, etc.) and then combining the assigned weights to generate scores. In this example, a value of a score computed for each program represents a potential benefit to the user 104 in participating in a corresponding program.

At step 3, the server 110 generates and provides selection result data 906 to the device 130. The selection result data 906 identifies a ranking computed by the server 110 for the programs 904A based on the user data 902. As described throughout, the rankings represent a relative prediction by the server 110 that (i) the user 104 will benefit from participation in a corresponding program (e.g., based on the user's interests and goals) and (ii) the user's participation will satisfy research requirements for the program and/or advance objectives of the program (e.g., whether the user is likely to complete the program, whether the user is likely to comply with treatment protocols, whether the user will perform certain actions that are beneficial or detrimental to research objectives, etc.).

The user selects to enroll in one of the programs identified in the selection result data 906. In the example shown in FIG. 9, the user 104 selects to enroll in a program for the vaccine clinical trial (which the server 110 ranked as having the highest priority). As depicted in FIG. 1B, once the user 104 enrolls in the selected program, the server 110 provides a customized module for the selected program. The program module is customized for the user 104 and/or the device 130 and configured to improve user experience while participating in the program. For example, the server 110 can use settings, such as user engagement and user retention, to customize the manner by which the user interacts with the program to improve the likelihood of obtaining a successful outcome.

At step 4, the server 119 receives an indication 908 with new user information while the user 104 is enrolled in and/or participating in an active program (e.g., program for a vaccine clinical trial). The indication 908 includes a new disease diagnosis for nicotine addiction that the user 104 received after he/she enrolled in the active program. This information was not previously included in the user data 902 and therefore was not considered by the server 110 in prioritizing amongst the programs 904 in step 2. However, given that the new disease diagnosis may impact, for example, a user's preferences for program participation, the server 110 determines to update the prioritizations previously generated. In some instances, the server 110 determines that receiving an indication of a new disease diagnosis that is likely to impact user preferences for program participation may satisfy a condition associated with program changes for an active program. For example, the server 110 determines that the condition is satisfied if the new disease diagnosis is likely to, for instance, reduce the user's participation in the active program, materially change the user's needs from program participation, reduce the quality of research data collected from user participation, among other factors.

At step 5, while a user is enrolled and/or participating in an active program, the server 110 generates a re-prioritized list of programs 904B based on the new user diagnosis specified by the indication 908. As discussed in reference to step (2), the learning models 110C predict that programs 904B may be beneficial to user 104 based on the information specified by the user data 902. However, at the second time point ($T_2$), a program for smoke cessation study (which was previously ranked as second important) is now identified as the most important study given the user's new diagnosis relating to nicotine addiction. In this example, the server 110 selects this program as the most important based on determining that the user's interest may now be to reduce nicotine consumption, which has the highest likelihood of being successfully achieved through participation in the smoke cessation study.

At step 6, the server 110 generates and provides updated selection result data 910 to the device 130. The updated selection result data 910 identifies a new ranking computed by the server 110 for the programs 904B based on the user data 902 and the indication 908. The updated rankings represent a new prediction by the server 110 that, given the user's new disease diagnosis, his/her interests and goals from program participation may have changed, and as a result, he/she may benefit from adjusting participation from an active program (for the vaccine clinical trial) to another program for the smoke cessation study.

At step 7, the device 130 provides a user interface 912 that provides the user 104 with an updated list of programs and rankings that the server 110 generated based on the user's new disease diagnosis.

Figure 10:
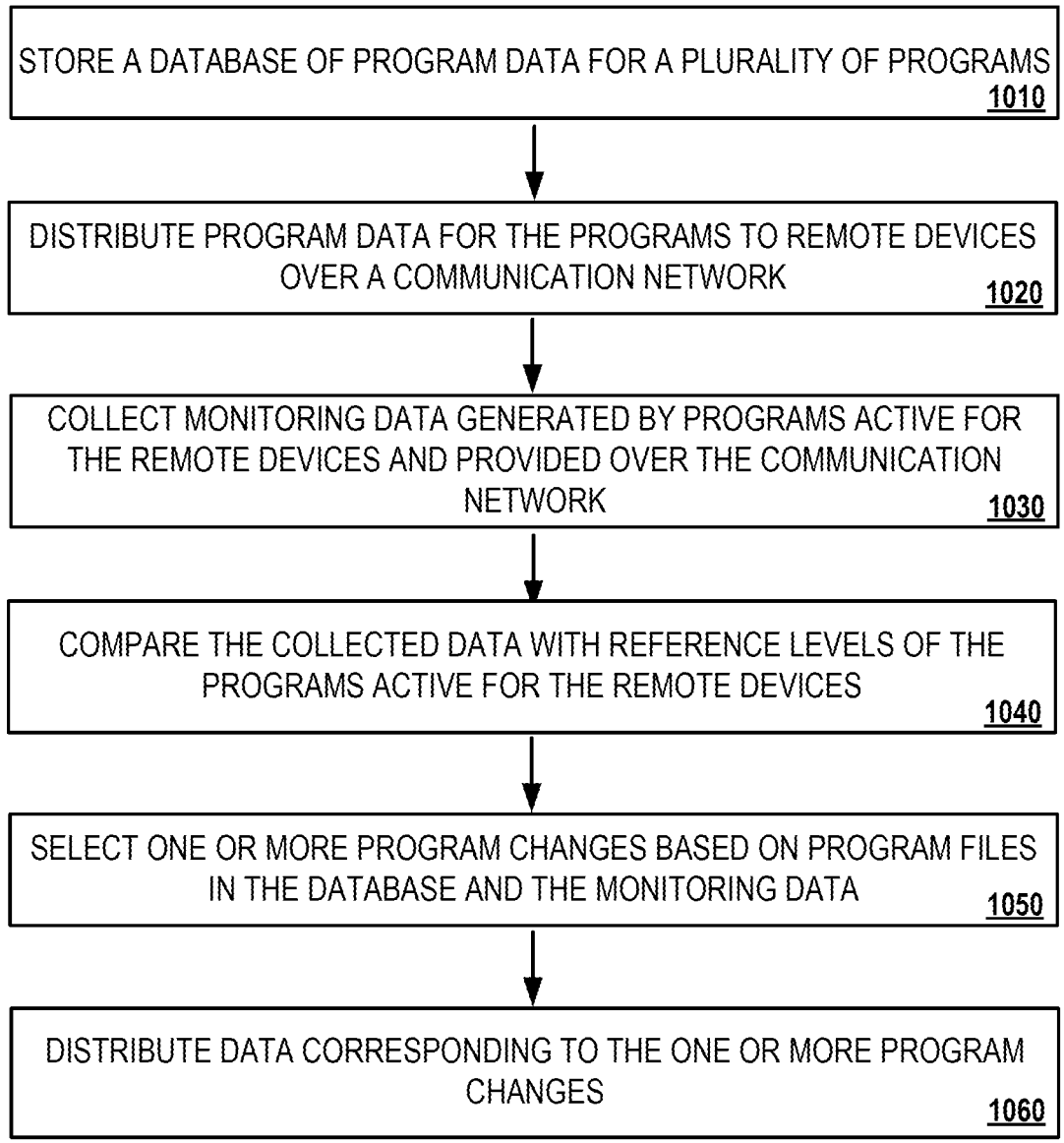
FIG. 10 illustrates an example of a process for prioritizing programs opportunities and monitoring active programs.

FIG. 10 illustrates an example of a process 1000 for prioritizing programs opportunities and monitoring active programs. The process 100 can be performed by one or more computers, such as a server system, e.g., the server 110. Briefly, the process 1000 includes storing a database of program data for a plurality of programs (1010), distributing program data for the programs to remote devices over a communication network (1020), collecting monitoring data generated by monitoring programs active for the remote device and provided over the communication network (1030), comparing the collected data with reference levels of the programs active for the remote devices (1040), selecting one or more program changes based on program files in the database and the monitoring data (1050), and distributing data corresponding to the one or more program changes (1060).

As discussed above, there are many situations in which devices and users begin participating in a monitoring program but then fail to perform the activities required for the monitoring program. This can lead to significant waste and overhead for client devices that may expend power, processing resources, storage space, and network bandwidth unnecessarily performing monitoring that is incomplete and will not serve its purpose (e.g., is too incomplete or inaccurate to allow events to be detected, or to be used in a research study, etc.). It also leads to inefficiency for the servers that handle the storage and processing of collected monitoring data, which are initiating interactions and responding to interactions that are not furthering the monitoring objective. The servers often are receiving, processing, and storing data unnecessarily, where the requirements for the data to be used in the monitoring program are not met and will not be met. Finally, this situation can jeopardize the entire monitoring program, e.g., not just for a few devices but for the overall scheme and all of the devices involved, which could lead to all of the monitoring work being done being wasted (e.g., for lacking the sufficient sample size for statistical significance, for lacking sufficient coverage in terms of geography or diversity in contexts and attributes being monitored, and so on.)

The server 110 and other management systems according to the techniques herein can address the inefficiencies and problems of prior systems by more actively evaluating the activity of devices and users in monitoring programs. This allows the system to manage both the individual monitoring actions of individual remote devices well but also to do so in a manner that preserves the validity and achieves the objectives of the overall monitoring schemes that devices and users are enrolled to participate in. For example, the server 110 can detect when a monitoring program of a device or user is ineffective and the server 110 can respond by identifying and initiating a change, in particular, to discontinue an ineffective monitoring program or to switch one active monitoring program for a different one that is better suited for the device, the user, and/or the needs of the monitoring programs. Other changes that the server 110 may identify and initiate are to add complementary monitoring programs. One example is the identification of monitoring programs that have overlapping data collection requirements, and so a second monitoring program can be added and made active for a device or user with minimal additional device overhead and user interaction, but which will add significant benefit to second monitoring program by adding the additional data.

Unlike application stores and many other systems, the management system that the server 110 implements actively checks whether the requirements of the various monitoring programs the server 110 manages are being fulfilled, and whether the capabilities and resources of the remote devices involved in monitoring are being used effectively. For example, the server 110 can detect when a device or user enrolled in a monitoring program is no longer complying with the requirements of a monitoring program (e.g., by not reporting data to the server 110, by providing incomplete or unreliable data to the server 110, if the device or software is incompatible with or incapable of performing the type of monitoring needed, if data represents a context or situation that is not needed or is excluded from monitoring, if a user does not provide inputs or carry out behaviors needed in the monitoring program, etc.). The server can also determine when the monitoring groups (e.g., the sets of participating devices and users) for the monitoring programs vary from their target characteristics (e.g., become too large, become too small, have a composition or level of diversity that does not meet desired characteristics, etc.). This allows the server 110 to manage the distribution and participation in monitoring programs at the level of the overall monitoring programs and for the entire ecosystem of monitoring programs. For example, the server 110 can determine when one monitoring program has a monitoring group that is larger than needed to meet its objective, and shift devices and users to other programs that are in need of more participants. Similarly, the server 110 can determine when a device or user enrolled in a monitoring program is performing effectively, but that a different monitoring program would derive much greater value from the participation of that device or user. For example, the program profiles may show that the context, characteristics, or history of a device or user involved in a first program would actually provide much more benefit to a second program, and the server 110 can initiate changes to shift the device or user to the second program, e.g., by adding the second program to be active alongside the first program, by ending participation in the first program and starting participation in the second program, etc.

The techniques discussed above can be used to score different programs using many factors, and the evaluation can be performed repeatedly (e.g., periodically, in response to a change in compliance for a device or user, when the program profiles or user profiles change, when monitoring programs become available or are discontinued, etc.). The scores may change from time to time, which can show that a change in monitoring program may be beneficial (e.g., for a device, user, provider of the monitoring program, etc.). This helps the server 110 reallocate the limited processing resources and time that devices have to contribute to the monitoring programs that will produce the greatest benefits and highest efficiency.

The process 1000 can be used by a system, such as the server 110, that is configured to create, recommend, and distribute the software, configuration data, and other content of different programs to remote devices over communication networks, such as the Internet. The programs can be programs that involve repeated, ongoing actions of users and their devices. For example, programs may involve devices taking measurements, monitoring measured values and taking actions in response to detecting certain conditions, reporting collected data to the server 110, providing interactions with users (e.g., prompts, surveys, notifications or alerts, user interfaces, etc.), and so on. Programs may also request or require user actions, including user interaction with their devices (e.g., play a game, complete a survey, and so on).

In the healthcare context, a variety of programs can be provided. Examples of health programs include research studies, classes/seminars on health topics (e.g., fitness, nutrition, tobacco cessation, stress management), exercise programs, chronic disease self-management tools, among others. Programs that are predicted to be useful for a user can be prioritized over other programs that are unlikely to be useful so that the user is provided with a customized experience that is tailored to his/her specific needs or interests.

The programs can be designed and implemented to monitor, maintain, and/or improve a user's health and wellness. This includes programs designed to help treat or manage diseases or health conditions, e.g., heart disease, diabetes, cancer, etc. Different programs can be designed and provided for different health conditions and for different types of patients (e.g., different ages, different severities of disease, etc.). The programs may also be used to provide digital therapeutics, including evidence-based therapeutic interventions driven by software programs to prevent, manage, or treat a medical disorder or disease. The programs can be configured to provide contextually relevant interventions to support the health and wellness of a user, can provide adaptive, personalized interventions including content and interactions to improve health of a user.

In more detail, the process 1000 includes storing a database of program data for a plurality of programs (1010). The server 110 can store program data for each of a plurality of programs that involve monitoring using remote devices. As discussed throughout, the program data can include a program profile indicating characteristics of each program and configuration data for configuring a remote device to carry out monitoring for the program. For example, referring back to FIG. 1A, the server 110 can store program data in a program database 110A. The program database 110A can store a list of programs available through the software platform (including programs for which program opportunities are identified). In some instances, the configuration data for the programs causes remote devices to configure sensors and user interfaces to perform interactions of the respective programs. For example, referring back to FIG. 1B, configuration data may relate to information specified by the customized program module 110B.

Process 100 includes distributing program data for the programs to remote devices over a communication network (1020). The server 110 can selectively distribute configuration data for programs to remove devices over a communication network. For example, as shown in FIG. 1A, the server 110 can distribute selection result data 106 with a list of programs selected for prioritization to device 130 of user 104 over a WLAN-based network.

Process 1000 includes collecting monitoring data generated by programs active for the remote device and provided over the communication network (1030). The server 110 can collect monitoring data that is generated by programs active for remote devices and is provided over a communication network. For example, referring back to FIG. 7, the server 110 can obtain collected data 706 from the device 130 while the user is enrolled in and/or participating in program 704A (an example of an active program). As shown in FIG. 7, the collected data 706 can include data relating to the user's participation in an active program, such as sensor data collected by the device 130, data representing user input through an application (e.g., survey input), or other associated context information associated with user participation in a program. In some instances, the monitoring data can also include user profile data 706B, which may include, for example, user interests, user availability, user attributes, genomics information, among other types of information.

Process 1000 includes comparing the collected data with reference levels of the programs active for the remote devices (1040). The server 110 can compare the collected monitoring data with reference levels corresponding to the programs active for the remote devices to identify a subset of the remote devices requiring a change.

A major role of the server 110 in administering and managing monitoring programs across a large set of devices is to detect when the set of monitoring programs that a device or user participates in should be changed. The server 110 detects when individual devices or users are not complying with the requirements of the monitoring program(s) they are enrolled in, or even when the pattern or trend of data received is indicative of likely future failure to meet the requirements. The server 110 can store and access the program profiles and other data specifying the activities and data collection of each monitoring program to determine the reference levels used for comparison. For example, one program may require sensor data provide each day while a second program may require sensor data to be uploaded only once per week. The server 110 determines, for each program, the reference levels that represent the requirements or standards for that particular program. The server 110 then compares the results achieved (e.g., data collection events, content of collected data, timing and frequency of communication, user activities indicated by the collected data, etc.) for the devices and users that are enrolled in a program with the reference levels representing the requirements of the program. This allows the system 110 to perform customized evaluation, on an ongoing basis, for each of the many monitoring programs that the server manages and oversees, allowing the server 110 to detect and address mismatches between programs and users and devices as they arise. When the server 110 detects one of many different conditions that indicate a change is appropriate, the server 110 can identify the specific type of change to be made for a specific remote device and user, such as to add a monitoring program for the device or user or to use a different program in place of a currently active program.

As described throughout, a program change may include ending an active program, adding a new program for user participation in parallel with participation in the active program, replacing user participation in the active program with a new program, among others. In some instance, the program change may adjust user participation in the active program, for example, by adjusting the manner of interacting with the user through a device application, adjusting a user goal associated with the active program, adjusting a performance objective for the user in the active program, adjusting the data being monitored by the application, or adjusting the type of user input accepted from the user.

In the example depicted in FIG. 7 illustrates an example of a program change in which the user is provided with a recommendation to enroll in a newly available program that the server 110 determines is more likely to be aligned with user interests and has a higher likelihood of user participation leading to a user meeting a performance objective. In this example, the user 104 can either enroll in the new program in parallel with the active program or replace participation in the active program with participation in the new program. In other examples of program changes, a user may adjust the level of interacting with an active program (e.g., increasing or reducing the amount of hours spent in participating in an active program), adjusting the types of actions performed for user participation (e.g., completing a different subset of participant actions specified by a program), among others.

Devices included in the selected subset can be devices for users that may benefit from a change to one or more active programs. As described throughout, the change can be based on various indicators or factors, such as an active program not providing benefit to the user, the user underperforming in an active program, a change in research prioritization, loss of user interest, participation, interaction, or engagement in an active program, among others. In such scenarios, the server 110 determines that a program change may improve user experience in program participation.

The server 110 can use different types of evaluations and/or assessments of the collected monitoring data to determine that a program change may be required. In some implementations, the server 110 assesses the collected monitoring data to determine whether active corresponding programs satisfy one or more conditions. The conditions can be based on any of various factors, such as user compliance, health outcomes, computing resources, user behavior, data quality (e.g., accuracy, completeness, precision), user availability, user burden, new programs becoming available, user health status change, user goals, progression of an active program, among others.

Each condition can indicate circumstances in which a certain type of program change can be used to improve program participation. Multiple conditions may exist for the same type of factor to represent different types of program changes. For example, if user compliance exceeds a threshold level, then a corresponding program change may be increase user participation to obtain additional high quality monitoring data that is likely to be useful to a researcher. In contrast, if user compliance is lower than another threshold level, then the corresponding program change may be to adjust the active program since the obtain the monitoring data collected through user participation may be too low quality to be useful to the researcher. As another example, if a user's performance during an active program is exceptionally good, then the program change may be to recommend a more challenging program since user's performance may have peaked and he/she is unlikely to further benefits from continued participation. In contrast, if the user's performance during an active program is below a specified threshold performance level, then the program change may be to recommend a different type of program since the user may not be motivated or engaged in the active program.

In various implementations, the server 110 can determine that a program change is required based on collected data that is collected, or in some instances, not collected. As described throughout, the server 110 can determine a program change is required if collected data satisfies a condition associated with reference levels for the collected data. In other instances, however, if data is not collected (e.g., because a user fails to participate in a program), then the server 110 can also use this information to determine that a program change is required. For example, if a user does not meet a performance target for an active program, then this information can be used to determine a program change for the active program. As another example, if the server 110 does not receive a certain type of data (e.g., survey data), then this can also be used to select a program change that removes the use of surveys as a way of enabling user interaction during the program.

In more detail, the server 110 can store a set of rules or models that assist the server 110 to evaluate the performance of each remote device and user involved in the monitoring programs. For each device or user, the server 110 can assess performance of and consider changes to active monitoring program that is active. An monitoring program can be considered "active" if the device or user is enrolled in or is subscribed to the program. Other examples of a program being active include if software for the program is downloaded or installed (and remains on the device), or if software or configuration data to carry out the monitoring is running or for which the device is configured to run, or otherwise if the device is configured to or scheduled to perform the data collection and interaction aspects of the monitoring program.

The server 110 can use a stored set of rules that can indicate conditions or triggering events that, if they occur, indicate that a change should be made to the set of programs that is active for a device of user. These rules can have customized thresholds or parameters for each program, or can be based on the scoring discussed above to customize the relevance of different programs with respect to individual devices and users. The server detects various conditions in which available resources to carry out monitoring become available (e.g., one monitoring program ends, freeing resources and time for another) or when monitoring is not effective (e.g., frequency, quality, completeness, accuracy, precision, reliability, variability, etc. of collected data or of user activities does not meet the levels needed for the monitoring program, often as determine through comparison to reference levels, such as ranges or thresholds determined for the specific programs individually). More generally, the rules can be used to determine when the objectives of a monitoring program are not furthering the objective of the monitoring program.

Another situation that the rules can be used to detect is when a goal of the participant is not satisfied. For example, a monitoring program may be intended to assist a user or device to achieve a goal, such as a health status in a therapeutic program, and if the program does not lead to further improvement (e.g., if the user's health or capability plateaus or declines), the server 110 can detect that a change in the program (e.g., a switch for a different program or addition of another program) may be needed. Thus, determining that a target outcome associated with the program is not achieved (e.g., health status, training goal, a target measurement level, level of ability, etc. that the program is trying to help the user achieve) can be a trigger for selecting and initiating a program change. Another situation is the end of a time period, such as the completion of or termination of a monitoring program, which can show that new availability is present to start a different monitoring program. Many other conditions can be defined in the rules, and the conditions can be based on both characteristics of the users and the needs of the programs. For example, if a program needs 1000 participants, but 1500 have enrolled, the system 110 may detect that some of the enrolled participants may be better allocated to another program that has not yet met its minimum levels.

As another example, the server 110 can use machine learning models to process input data, such as characteristics of devices and/or users and measures of their behaviors and compliance with program requirements. From this input to the models, and potentially including data indicating trends or changes over time or even time series data showing changes over time, the models can predict a likelihood that a user will be compliant with specific program requirements or with a program as a whole. For example, the techniques discussed above about predicting compliance of users with program requirements can be used to repeatedly predict a user's future compliance at multiple points in time through the participation in a program, allowing the server 110 to detect when the likelihood of successful completion of the program falls below a threshold. This can prompt or trigger the server 110 to identify potential program changes (e.g., swapping one program for another, reducing the total number of monitoring programs active for the device or user, etc.) to increase the likelihood of successful compliance and completion, and to reduce wasted monitoring actions and inefficiency.

Process 1000 includes selecting one or more program changes based on program files in the database and the monitoring data (1050). The server 110 may select one or more program changes base on program profiles in a database and monitoring data collected by a subset of remote devices identified as requiring a program change. The server 110 may use the reference levels corresponding to active programs to determine if and/or when a program change may be beneficial to a user or researcher. In some instances, the server 110 compares user interactions detected through remote devices to reference levels to determine whether to initiate a program change. The server 110 may asses user interactions to determine whether a condition associated with a program is satisfied. In such examples, the conditions may be used to trigger selection of a program change. For example, a reference level for a program includes a condition specifying a compliance requirement associated with participation in the program. In this example, the server 110 can determine that a series of user interactions for a user may indicate that the user has not satisfied the compliance requirement. The server 110 can then select a program change that involves recommending a new program for participation. The server 110 then distributes the selected program for output based on the selected program change.

Process 1000 includes distributing data corresponding to the one or more program changes (1060). The server 110 can distribute data indicating program changes to each of the subset of remote devices requiring a program change. The server 110 communicates the program change to applications on the remote devices that cause the applications to adjust user interfaces. For example, referring back to FIG. 1B, the server 110 can provide a customized program module 110D that can adjust user interfaces in various ways, such as adjusting the type of content provided to the user while participating in a program, an arrangement of content provided, the prioritization amongst different types of content, how content is provided through the interface, among others. In other examples, the server 110 provides an indication of programs that are available for enrollment, as shown in FIG. 9.

In some instances, the distributed data corresponding to the one or more program changes involves providing indications of new programs that are re-prioritized based on information specified by monitored data. In the example depicted in FIG. 7, the server 110 distributes data to device 130 to provide interface 712 with a recommendation to enroll in program 704B. In this example, the distributed data causes an application on device 130 to generate a notification recommending program 704B and content associated with the program 704B (e.g., video data).

As described throughout, the server 110 can use various factors to determine when program changes are appropriate for users enrolled in and/or participating in active programs and the type of program changes to implement. For instance, in the example depicted in FIG. 7, the server 110 determines a program change may be beneficial based on a new program becoming available and being predicted to have a higher probability of enabling a user to meet a performance objective based on low engagement in an active program. In this example, the server 110 selects a program change based on monitoring data collected from the user while participating in the active program and the user's performance in the active program. In contrast, in the example depicted in FIG. 8, the server 110 determines a program change may be beneficial based on a new research prioritization of a researcher managing an active program, and the new research prioritization indicating that user participation in a new program may provide greater research value to the researcher compared to user participation in the active program. In this example, the server 110 also determines that the new program aligns with user interests and/or does not present a significant user burden so the change in participation may mutually benefit both the researcher and user. In the example depicted in FIG. 9, the server 110 determines that a program change may be beneficial based on changes to user's health condition, which is likely to then change a user's preferences for program participation. In this example, the server 110 re-prioritizes a list of available programs based on the changes to the user's health condition so that the program prioritization data more accurately reflects current user preferences and/or user needs.

Various implementations of the systems and methods described here can be realized in digital electronic circuitry, integrated circuitry, especially designed ASICs (application specific integrated circuits), computer hardware, firmware, software, and/or combinations of such implementations. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor and can be implemented in a high-level procedural and/or object-oriented programming language, and/or in assembly/machine language. As used herein, the terms "machine-readable medium" "computer-readable medium" refers to any computer program product, apparatus and/or device, e.g., magnetic discs, optical disks, memory, Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device, e.g., a CRT (cathode ray tube) or LCD (liquid crystal display) monitor for displaying information to the user and a keyboard and a pointing device, e.g., a mouse or a trackball by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input.

The systems and techniques described here can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the systems and techniques described here, or any combination of such back end, middleware, or front end components. The components of the system can be interconnected by any form or medium of digital data communication, e.g., a communication network. Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

A number of embodiments have been described. Nevertheless, it will be understood that various modifications can be made without departing from the spirit and scope of the invention. In addition, the logic flows depicted in the figures do not require the particular order shown, or sequential order, to achieve desirable results. In addition, other steps can be provided, or steps can be eliminated, from the described flows, and other components can be added to, or removed from, the described systems. Accordingly, other embodiments are within the scope of the following claims.

What is claimed is:

1. A method performed by one or more computers, the method comprising:
   storing, by the one or more computers, program data that describes each of multiple monitoring programs designed to collect data from devices over a communication network, wherein the monitoring programs are respectively configured to collect data for different health research studies, and wherein the program data indicates researcher preferences indicating an importance of different user characteristics to the different health research studies;
   receiving, by the one or more computers, monitoring data collected by remote devices about their respective users over a period of time, wherein the monitoring data for each of the remote devices is collected for one or more of the monitoring programs active at the remote device, and wherein at least some of the remote devices have different monitoring programs active to collect data for the corresponding health research studies;
   based at least in part on the monitoring data and the stored program data, evaluating, by the one or more computers, the monitoring programs that are active among the remote devices;
   based on the evaluation, identifying, by the one or more computers, a particular remote device of the remote devices that satisfies one or more criteria for changing a set of monitoring programs active at the remote device;
   selecting, by the one or more computers, a program change for the particular remote device, wherein the program change is selected based on characteristics of a user of the particular remote device and the researcher preferences indicating the importance of different user characteristics to the different health research studies; and based on the selected program change, causing, by the one or more computers, the particular remote device to change the set of monitoring programs that are active at the particular remote device, including providing data to cause the particular remote device to (i) deactivate a monitoring program that was active at the particular remote device or (ii) activate a monitoring program that was not active at the particular remote device.

2. The method of claim 1, wherein causing the particular remote device to change the set of monitoring programs that are active comprises providing data to cause the particular remote device to deactivate a monitoring program that was active at the particular remote device.

3. The method of claim 1, wherein causing the particular remote device to change the set of monitoring programs that are active comprises providing data to cause the particular remote device to activate a monitoring program that was not active at the particular remote device.

4. The method of claim 1, wherein evaluating the monitoring programs comprises:

while a first monitoring program is active at the particular remote device, using the monitoring data to generate a first score for the first monitoring program and a second score for a second monitoring program that is not active at the particular remote device, wherein the first score and the second score are each based on a predicted level of compliance of a user of the particular remote device in performing data collection activities of the corresponding monitoring program; and prioritizing the first monitoring program and the second monitoring program based on the first score and the second score, and determining that the second monitoring program has a higher priority for the user than the first monitoring program;

wherein causing the particular remote device to change the set of monitoring programs that are active at the particular remote device comprises, based on determining that the second monitoring program has a higher priority for the user than the first monitoring program, causing the particular remote device to deactivate the first monitoring program and to activate the second monitoring program.

5. The method of claim 1, further comprising:

repeatedly evaluating compliance of a user of the particular remote device with the monitoring programs that are active at the particular remote device; and detecting, based on the evaluation of compliance of the user, that a likelihood of successful completion of a particular monitoring program active at the particular monitoring device is below a threshold;

wherein causing the particular remote device to change the set of monitoring programs that are active at the particular remote device is performed in response to detecting that the likelihood of successful completion of the particular monitoring program by the user is below the threshold.

6. The method of claim 1, wherein the program data for the respective monitoring programs indicates eligibility criteria for participation in the monitoring programs; and wherein evaluating the monitoring programs that are active among the remote devices comprises comparing, for each of the remote devices, relevance of the monitoring programs active for the remote device with relevance of other monitoring programs for which a user of the remote device satisfies the eligibility criteria.

7. The method of claim 1, wherein the program data for the respective monitoring programs includes configuration data for configuring a remote device to carry out monitoring for the program; and wherein providing the data to the particular remote device comprises providing the configuration data for a particular monitoring program that was not active at the particular remote device, wherein the configuration data enables the particular remote device to initiate monitoring for the particular monitoring program.

8. The method of claim 1, wherein selecting the program change comprises selecting the program change based on amounts of users enrolled in the respective monitoring programs.

9. The method of claim 1, wherein selecting the program change comprises selecting the program change based on (i) amounts of users enrolled in the respective monitoring programs and (ii) desired amounts of users to enroll in the respective monitoring programs.

10. The method of claim 1, wherein selecting the program change comprises selecting the program change based on differing amounts of benefit that data collection from the user of the particular device would provide to the different health research studies corresponding to the monitoring programs.

11. The method of claim 1, comprising identifying that a first monitoring program that is active for the particular device and a second monitoring program that is not active for the particular device have at least partially overlapping data collection requirements;

wherein selecting the program change comprises selecting to make the second monitoring program active at the particular device in addition to the first monitoring program, wherein the program change is selected is based on (i) an amount of additional device overhead or user interaction added by the second monitoring program relative to the first monitoring program and (ii) an amount of benefit that involving the user of the particular device in the second monitoring program would provide to a research objective of the health research study corresponding to the second monitoring program.

12. The method of claim 1, wherein a first monitoring program for a first health research study is active at the particular device;

wherein the method includes determining that the first health research study has a number of participants that is larger than needed to meet objectives of the first health research study;

wherein selecting the program change comprises selecting the program change to (i) deactivate the first monitoring program at the particular device based on determining that the first health research study has a number of participants that is larger than needed to meet objectives of the first health research study and (ii) activate a second monitoring program for a second health research study that has not reached a number of participants needed to meet objectives of the second health research study.

13. The method of claim 1, comprising determining that a group of users participating in a particular monitoring program does not have a composition or level of diversity that provides a predetermined set of characteristics;

wherein selecting the program change comprises selecting the program change based on (i) the determination that the group of users participating in the particular monitoring program does not have the composition or level of diversity that provides the predetermined set of characteristics and (ii) characteristics of the user of the particular device, wherein the program change includes activating the particular monitoring program active for the particular device or deactivating the particular monitoring program for the particular device.

14. A system comprising:
one or more computers; and
one or more non-transitory computer-readable media storing instructions that are operable, when executed by the one or more computers, to cause the one or more computers to perform operations comprising:
storing, by the one or more computers, program data that describes each of multiple monitoring programs designed to collect data from devices over a communication network, wherein the monitoring programs are respectively configured to collect data for different health research studies, and wherein the program data indicates researcher preferences indicating an importance of different user characteristics to the different health research studies;
receiving, by the one or more computers, monitoring data collected by remote devices about their respective users over a period of time, wherein the monitoring data for each of the remote devices is collected for one or more of the monitoring programs active at the remote device, and wherein at least some of the remote devices have different monitoring programs active to collect data for the corresponding health research studies;
based at least in part on the monitoring data and the stored program data, evaluating, by the one or more computers, the monitoring programs that are active among the remote devices;
based on the evaluation, identifying, by the one or more computers, a particular remote device of the remote devices that satisfies one or more criteria for changing a set of monitoring programs active at the remote device;
selecting, by the one or more computers, a program change for the particular remote device, wherein the program change is selected based on characteristics of a user of the particular remote device and the researcher preferences indicating the importance of different user characteristics to the different health research studies; and
based on the selected program change, causing, by the one or more computers, the particular remote device to change the set of monitoring programs that are active at the particular remote device, including providing data to cause the particular remote device to (i) deactivate a monitoring program that was active at the particular remote device or (ii) activate a monitoring program that was not active at the particular remote device.

15. The system of claim 14, wherein causing the particular remote device to change the set of monitoring programs that are active comprises providing data to cause the particular remote device to deactivate a monitoring program that was active at the particular remote device.

16. The system of claim 14, wherein causing the particular remote device to change the set of monitoring programs that are active comprises providing data to cause the particular remote device to activate a monitoring program that was not active at the particular remote device.

17. The system of claim 14, wherein evaluating the monitoring programs comprises:
while a first monitoring program is active at the particular remote device, using the monitoring data to generate a first score for the first monitoring program and a second score for a second monitoring program that is not active at the particular remote device, wherein the first score and the second score are each based on a predicted level of compliance of a user of the particular remote device in performing data collection activities of the corresponding monitoring program; and
prioritizing the first monitoring program and the second monitoring program based on the first score and the second score, and determining that the second monitoring program has a higher priority for the user than the first monitoring program;
wherein causing the particular remote device to change the set of monitoring programs that are active at the particular remote device comprises, based on determining that the second monitoring program has a higher priority for the user than the first monitoring program, causing the particular remote device to deactivate the first monitoring program and to activate the second monitoring program.

18. The system of claim 14, wherein the operations further comprise:
repeatedly evaluating compliance of a user of the particular remote device with the monitoring programs that are active at the particular remote device; and
detecting, based on the evaluation of compliance of the user, that a likelihood of successful completion of a particular monitoring program active at the particular monitoring device is below a threshold;
wherein causing the particular remote device to change the set of monitoring programs that are active at the particular remote device is performed in response to detecting that the likelihood of successful completion of the particular monitoring program by the user is below the threshold.

19. The system of claim 14, wherein the program data for the respective monitoring programs indicates eligibility criteria for participation in the monitoring programs; and
wherein evaluating the monitoring programs that are active among the remote devices comprises comparing, for each of the remote devices, relevance of the monitoring programs active for the remote device with relevance of other monitoring programs for which a user of the remote device satisfies the eligibility criteria.

20. One or more non-transitory computer-readable media storing instructions that are operable, when executed by one or more computers, to cause the one or more computers to perform operations comprising:
storing, by the one or more computers, program data that describes each of multiple monitoring programs designed to collect data from devices over a communication network, wherein the monitoring programs are respectively configured to collect data for different health research studies, and wherein the program data indicates researcher preferences indicating an importance of different user characteristics to the different health research studies;
receiving, by the one or more computers, monitoring data collected by remote devices about their respective users over a period of time, wherein the monitoring data for each of the remote devices is collected for one or more of the monitoring programs active at the remote device, and wherein at least some of the remote devices have different monitoring programs active to collect data for the corresponding health research studies;

based at least in part on the monitoring data and the stored program data, evaluating, by the one or more computers, the monitoring programs that are active among the remote devices;

based on the evaluation, identifying, by the one or more computers, a particular remote device of the remote devices that satisfies one or more criteria for changing a set of monitoring programs active at the remote device;

selecting, by the one or more computers, a program change for the particular remote device, wherein the program change is selected based on characteristics of a user of the particular remote device and the researcher preferences indicating the importance of different user characteristics to the different health research studies; and based on the selected program change, causing, by the one or more computers, the particular remote device to change the set of monitoring programs that are active at the particular remote device, including providing data to cause the particular remote device to (i) deactivate a monitoring program that was active at the particular remote device or (ii) activate a monitoring program that was not active at the particular remote device.

* * * * *